United States Patent
Chen et al.

(10) Patent No.: US 10,324,222 B2
(45) Date of Patent: Jun. 18, 2019

(54) METHODS AND SYSTEMS EMPLOYING NMR-BASED PREDICTION OF PORE THROAT SIZE DISTRIBUTIONS

(71) Applicant: HALLIBURTON ENERGY SERVICES, INC., Houston, TX (US)

(72) Inventors: Songhua Chen, Katy, TX (US); Wei Shao, Conroe, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/023,522

(22) PCT Filed: Feb. 26, 2015

(86) PCT No.: PCT/US2015/017790
§ 371 (c)(1),
(2) Date: Mar. 21, 2016

(87) PCT Pub. No.: WO2016/137472
PCT Pub. Date: Sep. 1, 2016

(65) Prior Publication Data
US 2016/0370492 A1 Dec. 22, 2016

(51) Int. Cl.
*G01R 33/44* (2006.01)
*G01V 3/32* (2006.01)
(Continued)

(52) U.S. Cl.
CPC .............. *G01V 3/32* (2013.01); *E21B 47/04* (2013.01); *E21B 47/0905* (2013.01);
(Continued)

(58) Field of Classification Search
CPC ......... G01N 24/081; G01N 15/08; G01V 3/32
See application file for complete search history.

(56) References Cited

U.S. PATENT DOCUMENTS 6,008,645 A * 12/1999 Bowers ............... G01V 3/14
250/253
6,247,542 B1 * 6/2001 Kruspe ............... E21B 33/1243
166/66
(Continued)

OTHER PUBLICATIONS

Rollin Brant, "Forward Selection", Mar. 24, 2004, The Univeristy of British Columbia, https://www.stat.ubc.ca/~rollin/teach/643w04/lec/node41.html, p. 1.*
(Continued)

*Primary Examiner* — John E Breene
*Assistant Examiner* — Christine Y Liao
(74) *Attorney, Agent, or Firm* — Gilliam IP PLLC

(57) ABSTRACT

Systems, methods, and software for predicting a pore throat size distribution are described. A representative method includes obtaining a nuclear magnetic resonance (NMR) relaxation-time distribution data set. The method also includes training a radial basis function (RBF) model based on the NMR relaxation-time distribution data set and a measured pore throat size distribution data set. The method also includes obtaining a subsequent NMR relaxation-time distribution data set. The method also includes employing the trained RBF model to predict a pore throat size distribution data set based at least in part on the subsequent NMR relaxation-time distribution data set. The method also includes storing or displaying a predicted pore throat size distribution corresponding to the predicted pore throat size distribution data set. The predicted pore throat size distribution is associated with a rock sample or subsurface formation volume.

22 Claims, 11 Drawing Sheets

(51) Int. Cl.
| | |
|---|---|
| *E21B 47/04* | (2012.01) |
| *E21B 49/00* | (2006.01) |
| *G01N 24/08* | (2006.01) |
| *E21B 47/09* | (2012.01) |
| *E21B 49/02* | (2006.01) |
| *G01V 3/38* | (2006.01) |
| *G01N 15/08* | (2006.01) |

(52) U.S. Cl.
 CPC .............. *E21B 49/00* (2013.01); *E21B 49/02* (2013.01); *G01N 24/081* (2013.01); *G01R 33/448* (2013.01); *G01V 3/38* (2013.01); *G01N 15/088* (2013.01)

(56) References Cited

U.S. PATENT DOCUMENTS

| | | | | |
|---|---|---|---|---|
| 6,337,568 | B1* | 1/2002 | Tutunji | G01N 24/081 324/300 |
| 2003/0128032 | A1* | 7/2003 | Heaton | G01V 3/32 324/303 |
| 2005/0206378 | A1* | 9/2005 | Hamdan | G01V 3/32 324/303 |
| 2005/0242807 | A1 | 11/2005 | Freedman | |
| 2009/0125239 | A1* | 5/2009 | Niemeyer | G01N 24/081 702/11 |
| 2010/0259258 | A1 | 10/2010 | Fransson et al. | |
| 2012/0065888 | A1 | 3/2012 | Wu et al. | |
| 2012/0241149 | A1 | 9/2012 | Chen et al. | |
| 2014/0055134 | A1 | 2/2014 | Fordham et al. | |
| 2014/0132259 | A1 | 5/2014 | Song | |

OTHER PUBLICATIONS

PCT International Search Report and Written Opinion, dated Oct. 30, 2015, Appl No. PCT/US2015/017790, "Methods and Systems Employing NMR-Based Prediction of Pore Throat Size Distributions," Filed Feb. 26, 2015, 10 pgs.

Anand, V. et al., "Predicting Effective Permeability to Oil in Sandstone and Carbonate Reservoirs From Well-Logging Data", SPE Reservoir Evaluation & Engineering v. 14(6), SPE-134011-PA, 2011, pp. 750-762.

Clerke, Edward A. et al., "Application of Thomeer Hyperbolas to Decode the Pore Systems, Facies and Reservoir Properties of the Upper Jurassic Arab D Limestone, Ghawar Field, Saudi Arabia: A "Rosetta Stone" Approach", GeoArabia 13(4), 113-160, 2008, 48 pgs.

Clerke, Edward A. , "Permeability and Microscopic Displacement Efficiency of M_1 Bimodal Pore Systems in Arab-D Limestone", SPE 105259, presented at the Middle East Oil and Gas Show, Bahrain, 2007, 12 pgs.

Coates, G.R. et al., "The MRIL in Conoco 33-1, An Investigation of a New Magnetic Resonance Imaging Log", Paper DD, presented at 32nd SPWLA Annual Logging Symposium, Midland, TX, USA, Jun. 16-18, 1991, SPWLA-1991-DD, 1991, 24 pgs.

Gao, Bo et al., "New Method for Predicting Capillary Pressure Curves From NMR Data in Carbonate Rocks", paper 2011-HH, presented at SPWLA 52nd Annual Logging Symposium, Colorado Springs, CO, USA May 14-18, 2011, SPWLA-2011-HH, 2011, 11 pgs.

Gomaa, N. et al., "Case Study of Permeability, VUG Quantification, and Rock Typing in a Complex Carbonate", SPE 102888 presented at 2006 SPE ATCE, San Antonio, TX, USA, Sep. 24-27, 2006, 10 pgs.

Kayser, Andreas et al., "A-Closer-Look-at-Pore-Geometry", Oilfield Review, Spring 2006, 2006, pp. 4-13.

Swanson, B.F. , "A Simple Correlation Between Permeabilities and Mercury Capillary Pressures", JPT, 33(12), SPE-8234-PA, 2488-2504, 1981, 7 pgs.

Thomeer, J.H. , "Air Permeability as a Function of Three Pore-Network Parameters", JPT, 53(4), SPE-10922-PA, 809-814, 1983, 6 pgs.

EP Application Serial No. 15883566.0, Extended European Search Report, dated Aug. 14, 2018, 6 pages.

Trevizan, et al., "Method for Predicting Permeability of Complex Carbonate Reservoirs Using NMR Logging Measurements", Petrophysics, vol. 55 No. 3, Jun. 2014, pp. 240-252.

\* cited by examiner

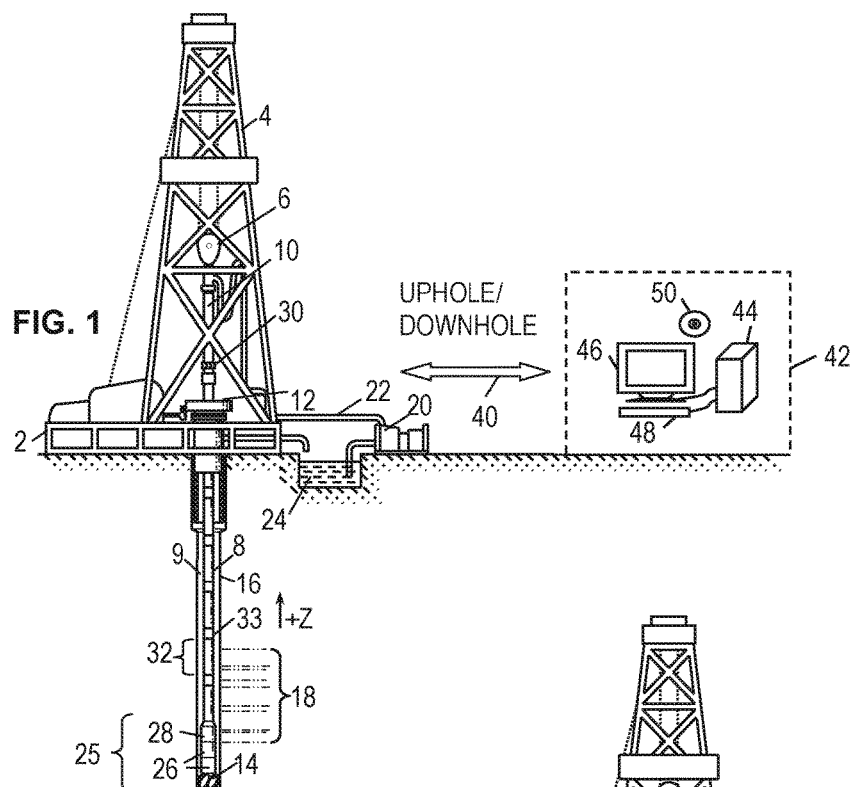
FIG. 1
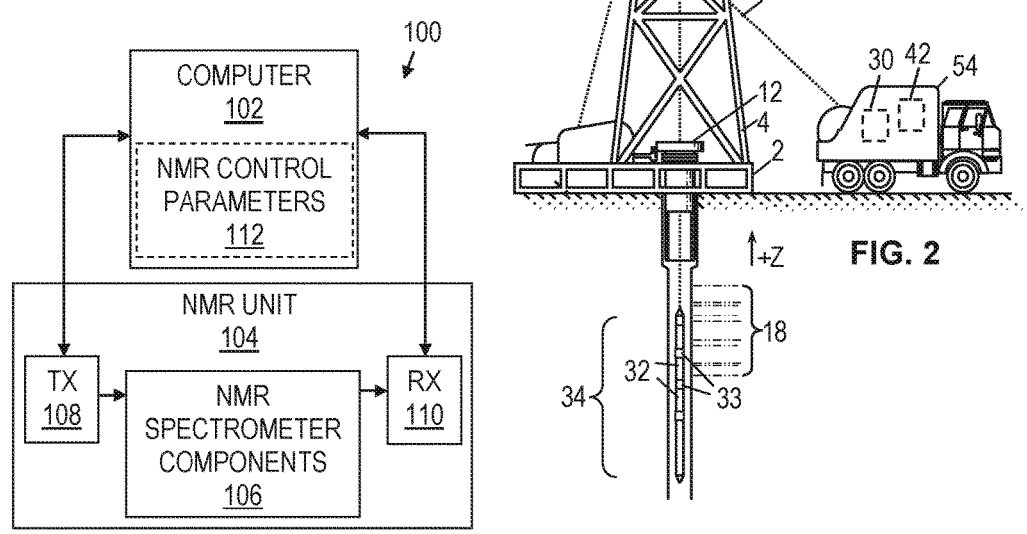
FIG. 3
FIG. 2

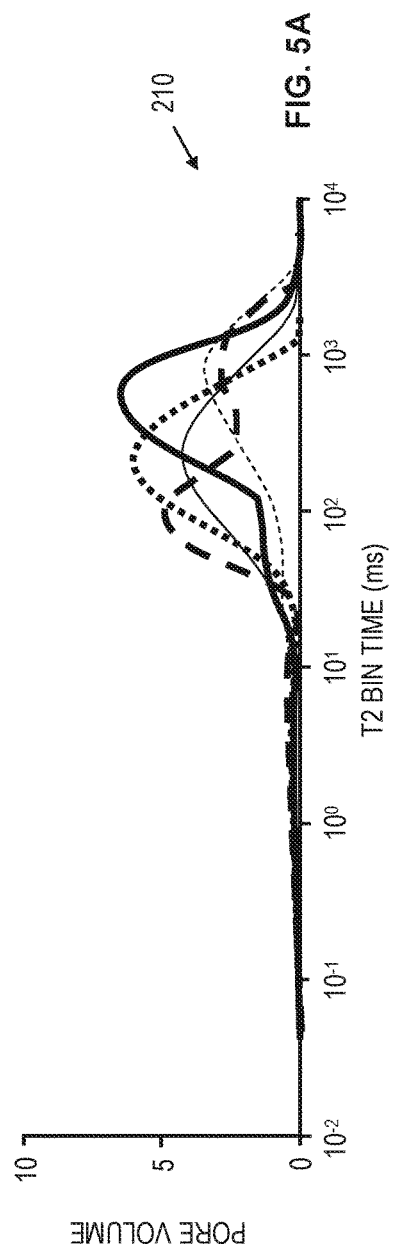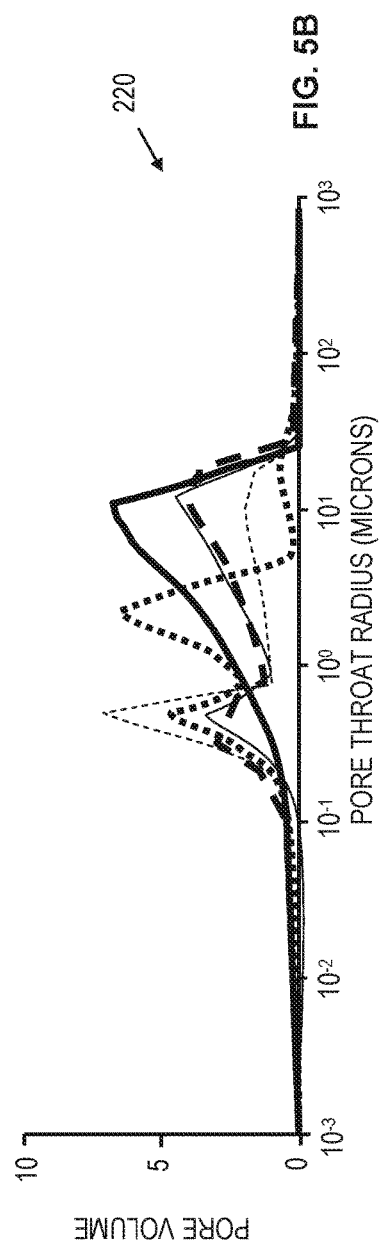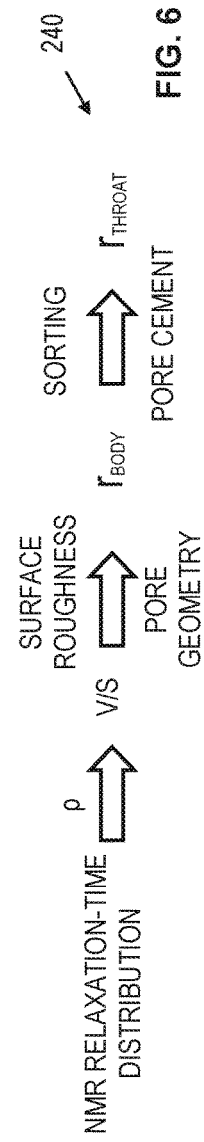

METHODS AND SYSTEMS EMPLOYING NMR-BASED PREDICTION OF PORE THROAT SIZE DISTRIBUTIONS

BACKGROUND

The efficiency of oil field operations such as drilling, well completion, and production depends on obtaining a suitable understanding of the structure and properties of the geological formations in the region of interest. To this end, oilfield operations perform various types of formation analysis using seismic surveys, downhole tools, and laboratory tools operating on samples retrieved to the surface. One example of formation or rock sample analysis involves nuclear magnetic resonance (NMR) phenomena.

NMR tools, whether embodied as a downhole tool or a laboratory instrument, generally include a magnet assembly that produces a static magnetic field ($B_0$), and a coil assembly that generates a perturbing magnetic field ($B_1$), usually in the form of an electromagnetic radio frequency (RF) pulse sequence. With suitable signal frequencies and field strengths, hydrogen nuclei can be induced to create a sequence of echoes that decay ("relax") in a characteristic fashion that represents an ensemble of spins de-phasing from each other. The decay rate is affected by the species of the spins and the local field homogeneity in the vicinity of the spins. The local field heterogeneity in reservoir rocks is primarily due to pore geometry, multi-phase fluid distribution, and the matrix minerals. A range of pore sizes, the surrounding matrix mineral distributions, and the fluid distribution in pore spaces results in multiplicity of relaxation times. With antennas to detect the echo sequence and processors to analyze the sequence, NMR tools can derive a spin-spin relaxation time ($T_2$) distribution for a sample volume. Similarly, NMR tools can also detect the interaction of spins with the surrounding material (lattice), and derive a spin-lattice relaxation time ($T_1$) distribution. Such distributions can each be correlated with various formation characteristics including pore size distribution and porosity distributions, among others.

In complex formations, particularly for carbonates, the pore structure is highly heterogeneous. This heterogeneity makes it difficult to establish analytical or empirical expressions that correlate well logging measurements with key "second order" material properties, such as pore connectivity, pore type, capillary pressure, or permeability. (Such properties are fundamental to determining efficient reservoir production strategies.) A typical approach for developing a petrophysical interpretation model for heterogeneous reservoirs uses a large number of core samples; this approach recognizes that a small number of samples fail to represent the reservoir rock system. However, it has been determined that, even with a large number of samples, it is difficult to find correlations that can serve as the basis for useful predictions and understanding of reservoir behavior.

BRIEF DESCRIPTION OF THE DRAWINGS

Accordingly, there are disclosed herein methods and systems to predict pore throat size distributions using nuclear magnetic resonance (NMR) data. In the figures:

FIG. 1 is a schematic diagram showing an illustrative logging-while-drilling (LWD) survey environment.

FIG. 2 is a schematic diagram showing an illustrative wireline logging survey environment.

FIG. 3 is a block diagram showing an illustrative NMR system.

FIGS. 5A and 5B are plots showing comparative NMR and pore throat size information.

FIG. 6 is a diagram showing an illustrative correlation between NMR data and pore throat size.

Figure 4:
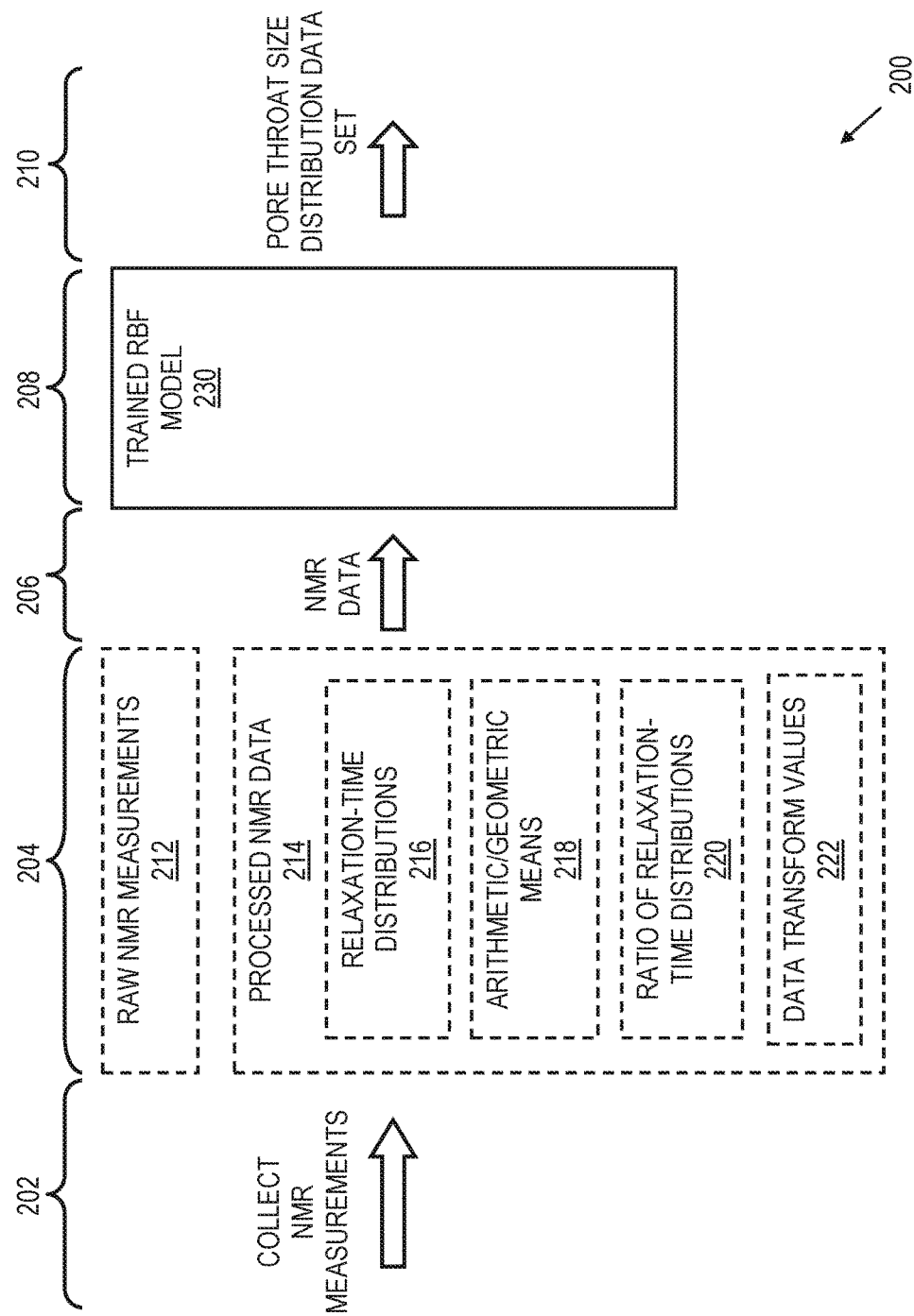
FIG. 4 is a block diagram showing an illustrative process for predicting pore throat size distributions.

It should be understood, however, that the specific embodiments given in the drawings and detailed description below do not limit the disclosure. On the contrary, they provide the foundation for one of ordinary skill to discern the alternative forms, equivalents, and other modifications that are encompassed in the scope of the appended claims.

DETAILED DESCRIPTION

Disclosed herein are methods and systems to predict pore throat size distributions using nuclear magnetic resonance (NMR) data applied to a radial basis function (RBF) model. In at least some embodiments, the RBF model outputs a predicted pore throat size distribution data set corresponding to values that directly represent a predicted pore throat size distribution. In such case, the NMR data applied to the RBF model corresponds to values that directly represent a NMR relaxation-time distribution. Further, the training data set for the RBF model may include training values that directly represent an NMR relaxation-time distribution and training values that directly represent a measured pore throat size distribution.

In alternative embodiments, the RBF model outputs a predicted pore throat size distribution data set corresponding to data transform values (e.g., principal components or factors) that indirectly represent a predicted pore throat size distribution (i.e., a predicted pore throat size distribution can be reconstructed from the data transform values). In such case, the NMR data applied to the RBF model may correspond to data transform values that indirectly represent an NMR relaxation-time distribution. Further, the training data set for the RBF model may correspond to data transform values that indirectly represent an NMR relaxation-time distribution as well as data transform values that indirectly represent a measured pore throat size distribution.

Regardless of the particular data set output from the RBF model, a predicted pore throat size distribution associated with a rock sample or subsurface formation volume is obtained directly or indirectly from the output, and may be stored or displayed. An example display format may plot predicted pore throat size distributions as a function of measured depth. Further, predicted pore throat size distributions may be used to derive other parameters such as minimum entry pressure or permeability. In such case, a permeability log associated with a rock sample or subsurface formation volume may be obtained based on predicted pore throat size distributions. In at least some embodiments, predicted pore throat size distributions, parameters derived from predicted pore throat size distributions, and/or related logs are used to make reservoir development decisions (e.g., well placement, fracturing, perforation placement/spacing, treatments) and/or to direct downhole operations.

The disclosed methods and systems are best understood in an application context. Turning now to the figures, FIG. 1 shows an illustrative logging-while-drilling (LWD) environment. In FIG. 1, a drilling platform 2 is equipped with a derrick 4 that supports a hoist 6 for raising and lowering a drill string 8. The hoist 6 suspends atop drive 10 suitable for rotating the drill string 8 and lowering the drill string 8 through the well head 12. Connected to the lower end of the drill string 8 is a drill bit 14. As bit 14 rotates, it creates a borehole 16 that passes through various formations 18. A pump 20 circulates drilling fluid through a supply pipe 22 to top drive 10, down through the interior of drill string 8, through orifices in drill bit 14, back to the surface via the annulus 9 around drill string 8, and into a retention pit 24. The drilling fluid transports cuttings from the borehole 16 into the pit 24 and aids in maintaining the integrity of the borehole 16. Various materials can be used for drilling fluid, including oil-based fluids and water-based fluids.

In FIG. 1, logging tools 26 are integrated into a bottom-hole assembly 25 near the bit 14. As the bit 14 extends the borehole 16 through the formations 18, logging tools 26 collect measurements relating to various formation properties as well as the tool orientation and various other drilling conditions. Each of the logging tools 26 may take the form of a drill collar, i.e., a thick-walled tubular that provides weight and rigidity to aid the drilling process. For the present discussion, the logging tools 26 are expected to include an NMR logging tool that collects raw NMR measurements. The bottom-hole assembly 25 also may include a telemetry sub 28 to transfer raw NMR measurements or processed NMR data to a surface communication interface 30 and to receive commands from the surface. Example telemetry options include mud pulse telemetry, acoustic telemetry, electromagnetic telemetry, wired drill pipe telemetry, or a combination of telemetry options. The surface communication interface 30 forwards the raw NMR measurements or processed NMR data to and/or receives commands from a computer system 42 via a wired or wireless interface 40.

The computer system 42 may perform various operations such as providing commands for logging tools 26, storing raw NMR measurements or processed NMR data, further processing NMR measurements or NMR data, training an RBF model, employing a trained RBF model to predict a pore throat size distribution data set, deriving parameters from predicted pore throat size distributions corresponding to predicted pore throat size distribution data sets, and/or displaying data logs or other information to an operator. In at least some embodiments, the computer system 42 includes a processing unit 44 that performs various operations by executing software or instructions obtained from a local or remote non-transitory computer-readable medium 50. The computer system 42 also may include input device(s) 48 (e.g., a keyboard, mouse, touchpad, etc.) and output device(s) 46 (e.g., a monitor, printer, etc.) Such input device(s) 48 and/or output device(s) 46 provide a user interface that enables an operator to interact with the logging tools 26 and/or software executed by the processing unit 44. For example, the computer system 42 may enable an operator to select NMR logging options, to view raw NMR measurements, to view processed NMR data, to adjust RBF model training options, to adjust training data sets, to adjust inputs to a trained RBF model, to adjust data transform options, to adjust use of predicted pore throat size distributions, to adjust visualization options, and/or to perform other tasks.

In different embodiments, an NMR logging tool corresponding to logging tool 26 may include processing, storage, and/or other components to select pulse sequences, to store echo information (e.g., amplitude as a function of time), to calculate parameters derived from the stored echo information (e.g., a $T_1$ distribution, a $T_2$ distribution, a diffusion measurement, and/or a porosity), to update NMR logging operations based on the calculated parameters and/or to update NMR logging operations in response to commands from the surface. Such commands from the surface may be generated in response to programmed logging operations performed by computer system 42, parameters derived from collected echoes by computer system 42 or operator, and/or an operator otherwise selecting or entering logging control options via a user interface.

At various times during the drilling process, the drill string 8 may be removed from the borehole 16 as shown in FIG. 2. Once the drill string has been removed, logging operations can be conducted using a logging string (sonde) 34 suspended by a cable (wireline) 52 having conductors for transporting power to the logging string 34 and telemetry from the logging string 34 to the surface. In some embodiments, the logging string 34 may have pads and/or centralizing members to maintain logging tools 32 near the axis of the borehole as the logging string 34 is pulled uphole. The logging tools 32 may correspond to a variety of logging tools including an NMR logging tool with the same or similar features as the NMR logging tool described for logging tool 26. A logging facility 54 includes a surface communication interface 30 and a computer system 42 for receiving, storing, and processing raw NMR measurements or processed NMR data obtained by the logging tools 32. The computer system 42 of FIG. 2 may also send commands and/or logging control parameters to the logging tools 32, perform RBF model training, predict pore throat size distributions, and/or perform other operations as described herein.

Although the disclosed method and systems are directed to obtaining NMR data and employing an RBF model to predict a pore throat size distribution data set based on the obtained NMR data, it should be appreciated that other logging data may be collected and applied to an RBF model to predict a pore throat size distribution data set. For example, in some embodiments, gamma ray data in addition to NMR data is collected and applied to an RBF model to predict a pore throat size distribution data set. In such case, the logging tools 26 of FIG. 1 and the logging tools 32 of FIG. 2 may include a gamma ray logging tool as well as an NMR logging tool. Additionally or alternatively, other logging tools and corresponding measurements/logs may be used along with NMR data to predict pore throat size distributions.

FIG. 3 shows a block diagram of an illustrative NMR system 100. As shown, the NMR system 100 includes a computer 102 that provides NMR control parameters 112 to an NMR unit 104. In different embodiments, the components of NMR system 100 may be located at earth's surface (e.g., as part of an NMR facility or laboratory) or downhole (e.g., as part of logging tools 26 or 32). Alternatively, some of the components (e.g., computer 102) may be located at earth's surface while other components (e.g., NMR unit 104) are located downhole. Regardless of component location, the computer 102 directs the operations of the NMR unit 104 (e.g., a downhole tool or laboratory equipment), which includes a transmitter (TX) 108, a receiver (RX) 110, and NMR spectrometer components 106.

More specifically, the computer 102 is configured to provide commands, programming, and/or data to transmitter 108 of the NMR unit 104. The transmitter 108 may include a programmable pulse sequence device or storage, a radio frequency (RF) synthesizer, a phase shifter, a pulse gate, an amplifier, and/or other components. Further, in different embodiments, the NMR control parameters 112 enable adjustment of pulse sequences and receiver window options based on a default configuration, user selection, and/or calibration.

The NMR unit 104 also includes NMR spectrometer components 106 used for magnetic resonance operations. Examples of NMR spectrometer components 106 include one or more magnets, shim coils, probes/antennas, and/or field-frequency lock components. Further, the NMR spectrometer components 106 may include a duplexer that enables separation between transmission current and reception current. The receiver 110 of NMR unit 104 is configured to receive and decode magnetic resonance signals. The receiver 110 may include, for example, an analog-to-digital converter (ADC), filters, mixers, splitters, pre-amplifiers, and/or other components to receive magnetic resonance signals and recover measurement data. The raw NMR measurements or processed NMR data is output from the receiver 110 to computer 102 for storage, display, and/or analysis. In some embodiments, the computer 102 may further process raw NMR measurements or processed NMR data received from the NMR unit 104. Further, the computer 102 may predict pore throat size distributions as described herein, or may forward raw NMR measurements and/or processed NMR data to another computer that predicts pore throat size distributions.

FIG. 4 is a block diagram of an illustrative process 200 for pore throat size distribution prediction. As shown, the process 200 includes collecting NMR measurements at stage 202. As previously discussed, the NMR measurements may be collected by a LWD tool, a wireline tool, and/or an NMR laboratory tool. in at least some embodiments, the NMR measurements are collected at stage 202 by energizing and manipulating nuclear spins in a formation with a pulsed radio frequency (RF) magnetic field. Various pulse sequences i.e., series of RF pulses, delays, and other operations) can be used to collect the NMR measurements. Example pulse sequences include the CPMG sequence (in which the spins are first flipped to the plane perpendicular to the static magnetic field direction using a tipping pulse followed by a series of refocusing pulses), the Optimized Refocusing Pulse Sequence (ORPS) in which the refocusing pulses are less than 180°, a saturation recovery pulse sequence, and other pulse sequences.

At stage 204, the NMR measurements collected at stage 202 are conveyed as raw NMR measurements 212 and/or are processed. Examples of processed NMR data 214 include relaxation-time distributions 216 (e.g., $T_1$ or $T_2$ distributions), arithmetic or geometric means 218 (e.g., arithmetic or geometric means of $T_1$ or $T_2$ distributions), a ratio of relaxation-time distributions 220 (e.g., $T_1/T_2$), and data transform values 222 (e.g., principal components or factors for $T_1$ or $T_2$ distributions). The processed NMR data 214 represented in stage 204 may be derived by the same computer that predicts pore throat size distributions or by at least one other processing component (e.g., in a downhole logging tool, a laboratory computer, or another computer) that handles the NMR measurements collected at stage 202.

As an example of processing NMR measurements, NMR measurements collected at stage 202 may correspond to a spin-echo train that includes a series of multi-exponential decays. In such case, relaxation-time distributions represent a discrete population density of the decay rates extracted from the spin-echo train. More specifically, such NMR measurements can be described as multiple components resulting from multiple different relaxation times in the measured region. For example, the signal amplitude of the first echo may be expressed approximately by:

$$\phi(t=TE)=\Sigma_{i=1}^{N}\phi_i(TE), \qquad \text{Equation (1)}$$

where $$\phi_i(t) = c_i \exp\left(-\frac{t}{T_{2i}}\right). \qquad \text{Equation (2)}$$

Here, each of the N components has a respective amplitude, $\phi_i$, and a characteristic relaxation time, $T_{2i}$.

In some source rocks, some of the components (i<k) (those having the shortest relaxation times $T_{2i}$) decay too quickly to produce a measureable signal at t=TE. In such case, the measurable signal amplitude is the apparent porosity:

$$\phi_{app}(TE)=\Sigma_{i=k}^{N}\phi_i, \qquad \text{Equation (3)}$$

which is smaller than the total signal (total porosity):

$$\phi=\Sigma_{i=1}^{N}\phi_i. \qquad \text{Equation (4)}$$

The $T_2$ distribution derived from the NMR measurement can then be described as: $\phi$: {$\phi_i$ vs. $T_{2i}$, where i=k: N and $\phi_i$=0 for i<k}. Clearly, it is desirable to set the interecho time, TE, as short as possible in data acquisition, in order to be able to measure the short relaxation time components. However, the minimum TE is generally constrained by the hardware, available power, and operating frequency. Thus, the apparent porosity is still in deficit compared to the total porosity. This porosity deficit is, in general, not detrimental to the use of the method described in the invention, as long as the RBF model is generated with the NMR data having, similar characteristics. Thus, it is important that in such case, the NMR training data should be acquired with substantially same TE as that used in logging data acquisition. On the other hand, the difference between the NMR apparent porosity and the true total porosity can be used to aid pore throat size computation, as the missing porosity may be correlated partially with pore throat size. For example, an independent porosity measurement, such as a porosity derived from density logging, can he used an additional input to train the RBF model and to subsequently obtain pore throat size distribution predictions from an output of the RBF model.

At stage 206, NMR data representing the raw NMR measurements 212 and/or at least some of the processed NMR data 214 is forwarded to a trained RBF model 230 at stage 208. Various RBF model training options are available as described herein. In at least some embodiments, the trained RBF model 230 outputs a predicted pore throat size distribution data set represented at stage 210. The predicted pore throat size distribution data set of stage 210 directly or indirectly represents a predicted pore throat size distribution that may be stored or displayed. Additionally or alternatively, parameters derived from a predicted pore throat size distribution may be stored or displayed. Example parameters include minimum entry pressure and permeability.

In accordance with at least some embodiments, the trained RBF model 230 corresponds to an RBF model created by solving one or more inverse problems. Inverse problems encountered in well logging and geophysical applications may involve predicting the physical properties of some underlying system given an input data set. The plots 210 and 220 of FIGS. 5A and 5B show $T_2$ distributions and corresponding pore throat size distributions for five carbonate core samples. As can be discerned from plots 210 and 220, predicting pore throat size distributions from $T_2$ distributions is not straightforward and represents a non-linear correlation.

FIG. 6 is a diagram showing an illustrative correlation 240 between NMR data and pore throat size. In correlation 240, NMR data such as a $T_1$ or $T_2$ distribution is mapped to a pore body size distribution, V/S, according to:

$$\frac{1}{T_i \text{ or } T_{2,int}} \approx \rho \frac{S}{V},$$

where S is pore surface, V is volume, and $\rho$ is surface relaxivity. Because $\rho$ is mineral-dependent and fluid-dependent, NMR relaxation-time distributions are not necessarily linearly dependent on the pore volume to pore surface ratio. In addition to inhomogeneities for surface relaxivity, which may occur in complex mineralogy carbonate reservoirs, the correlation 240 includes mapping V/S to the radius of the pore bodies as a function of grain/pore geometries as well as the surface roughness. The correlation 240 also includes mapping the pore body size ($r_{body}$) to pore throat size ($r_{throat}$) as a function of sorting and pore cementation. For carbonates, chemical processes (e.g., dissolution and recrystallizing) result in mappings that are highly non-linear and heterogeneous. Therefore, it is often not possible to find a closed-form mathematical expression to include all of these non-linear effects.

Figure 7:
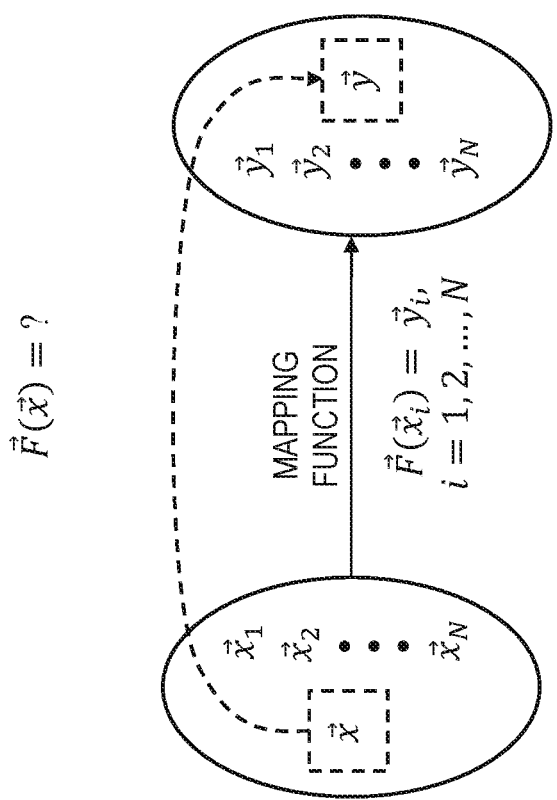
FIG. 7 is a diagram showing an illustrative mapping function.

Referring to FIG. 7, consider a database having used of distinct input data $\vec{x}_i \in R^n$ (i.e., the inputs are n-dimensional vectors) and a set of corresponding outputs, $\vec{y}_i \in R^m$, for i=1, . . . , N, where N is the number of cases in the database. The different cases in the database represent different states of the underlying physical system. In this notation, $\vec{y}_i$ values represent samples of the function that one wants to approximate (e.g., by a model), and values are the distinct points at which the function is given. The database is used to construct a mapping function such that $F(\vec{x}_i)=\vec{y}_i$, for =1, . . . , N. As used herein, the mapping function can be solved through the inverse problem of predicting pore throat size distributions for a formation based on available NMR data.

Figure 8:
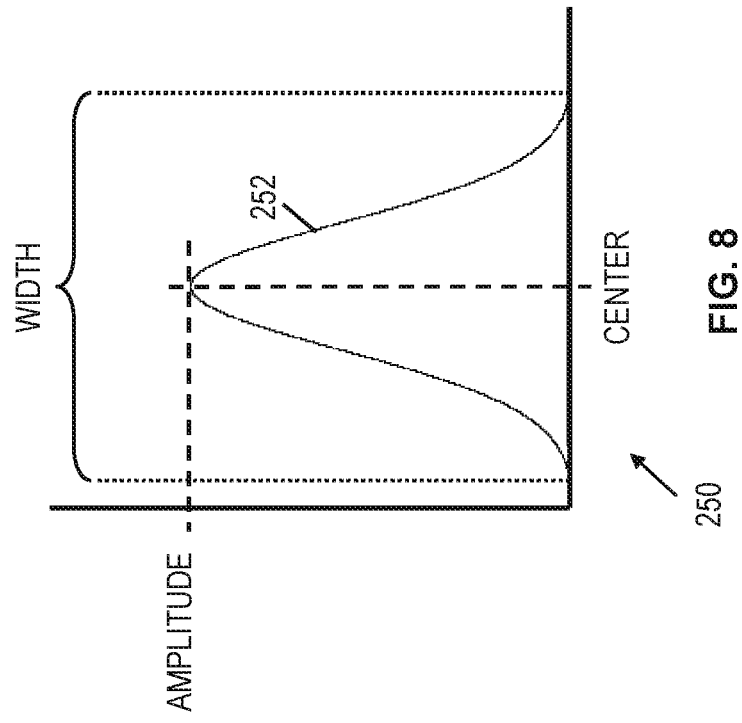
FIG. 8 is a graph showing an illustrative function used for RBF modeling.

In at least some embodiments, the trained RBF model 230 corresponds to a prediction model constructed from basis functions. Further, PCA may be applied to preprocess at least some of the model training data. FIG. 8 shows an illustrative basis function from which an RBF model may be constructed. In graph 250 of FIG. 8, the basis function corresponds to a Gaussian function having a given center, amplitude, and width. To concept of constructing an RBF model involves combining multiple basis functions having different characteristic parameters (e.g., center, amplitude, width, and sign) according to a set of predetermined rules. It should be appreciated that basis functions other than Gaussian functions may be used to construct an RBF model. Further, it should be appreciated that the rules for combining multiple basis functions to construct an RBF model may be adjusted. Such rules may include the number of basis functions to be used, characteristic parameter maximums, characteristic parameter minimums, characteristic parameter ranges, data normalization options, data fit options, etc. Various details for constructing an RBF model from basis functions are discussed later.

Typically, the NMR measurements represented in stage 202 are affected by noise, and the noise is introduced into the processed NMR data 214 derived from the NMR measurements. In some instances, important structures of the processed NMR data 214 are less affected by the noise, and these important structures can be used for training an RBF model. In addition, data within different types of processed NMR data 214 are often highly correlated, and thus contain redundancies that can unnecessarily increase the complexity of the RBF model 230. To account for these phenomena, PCA operations may be performed to reduce processed NMR data 214 (e.g., relaxation-time distributions) to a subset of key components. In at some embodiments, PCA operations provide a rank ordering of variances in at least some of the processed NMR data 214. The rank ordering can be structured such that principal components with larger associated variances represent important structure (signal), while those with lower variances represent noise or insignificant information.

Such PCA operations can be described as transforming a set of data vectors from an initial coordinate system to a new coordinate system. The new coordinate system can be defined such that when the data vectors are expressed in the new coordinate system all (or substantially all) significant variations among the data vectors are described by a reduced number of vector components. Thus, although the data vectors may have the same number of components in both coordinate systems, most of the vector components in the new coordinate system can be ignored or neglected; the retained vector components form a set of principal components that are used to analyze the data.

In some cases, the $k^{th}$ principal component is the $k^{th}$ component of a transformed data vector in the new coordinate system. The proportion of the total variance accounted for by the $k^{th}$ principal component can be:

$$\frac{\lambda_k}{\sum_{i=1}^{n} \lambda_i},$$

where $\lambda_i$, i=1, . . . , n are the eigenvalues of the covariance matrix of the training data set. Each of the eigenvalues quantifies the variance of the corresponding principal component.

Figures 9, 10:
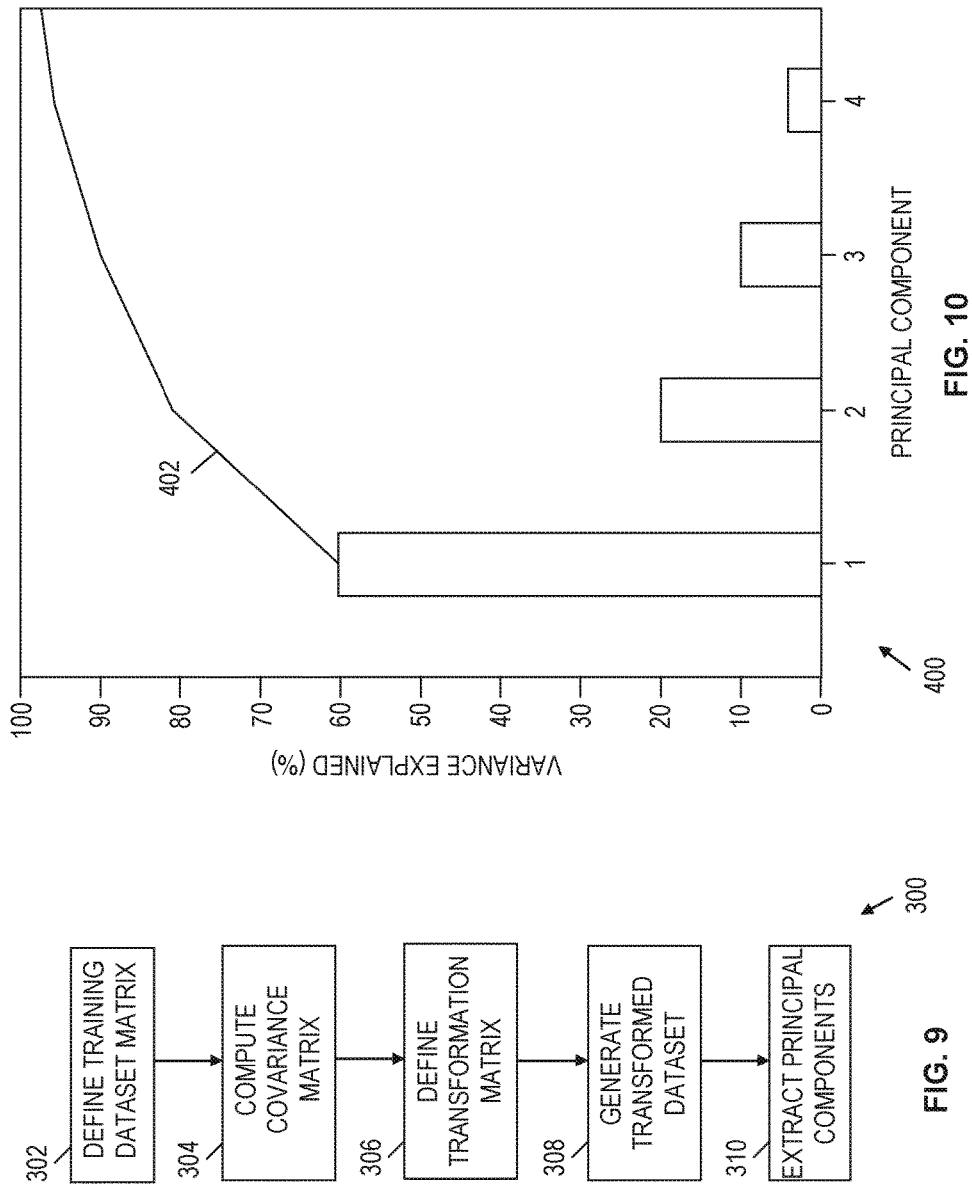
FIG. 9 is a diagram showing an illustrative principal component analysis (PCA) process.
FIG. 10 is a graph that shows illustrative data variance as a function of individual principal components.

Referring to FIG. 9, an example PCA process 300 can be used to generate sets of principal components from relaxation-time distributions, where each set of principal components represents a respective one of the relaxation-time distributions. The process 300 can include additional or different operations, and the operation can be performed in the order shown or in another order.

At block 302, a dataset matrix X is formed from the relaxation-time distributions. Each of the n relaxation-time distributions has p elements, so the dataset matrix X can be an n×p matrix (n rows, p columns), in which each of the relaxation-time distributions forms a respective row. The training dataset of relaxation-time distributions can be represented in another manner, using any suitable data format, data structure, or data type.

The relaxation-time distributions can include distributions of transverse relaxation times or longitudinal relaxation times obtained from NMR data. In some cases, the area integration of each distribution is normalized to a common normalizing value. For example, the normalizing value can be 1 or another constant value. To normalize a distribution, the values in the distribution can be multiplied or scaled uniformly so that the area of the scaled distribution is equal to the normalizing value.

At block 304, the eigenvectors of the covariance matrix C of dataset matrix X are determined. The covariance matrix C may be computed as $C=X^TX$, where $X^T$ is the transpose of the dataset matrix X, or the covariance matrix can be computed in another manner. In some instances, one or more of the eigenvectors can be obtained without explicitly computing the covariance matrix.

At block 306, a transformation matrix $W_L$ is formed, where $W_L$ is a p×l matrix whose columns are eigenvectors of the covariance matrix C. The transformation matrix $W_L$ can be formed from the l eigenvectors that correspond to the l largest eigenvalues of the covariance matrix C. The eigenvectors and eigenvalues of the covariance matrix C can be determined, for example, by conventional techniques for computing matrix eigenvectors and eigenvalues.

At block 308, the dataset matrix X is converted to a new coordinate system, resulting in a transformed matrix $T=XW_L$. At block 310, sets of principal components are extracted from the transformed matrix T. In at least some embodiments, the transformed matrix T is an n×l matrix, and the $i^{th}$ row contains a set of principal components corresponding to the $i^{th}$ relaxation-time distribution in the dataset matrix X. For example, the matrix element T(i,k) (the element at the $k^{th}$ column and $i^{th}$ row) can represent the $k^{th}$ principal components of the $i^{th}$ relaxation-time distribution.

In some embodiments, the data vectors (in the initial coordinate system) can be the $T_2$ distributions of a database corresponding to NMR measurements or related NMR data, and each data vector can have 27 or 54 components. In some cases, the relaxation-time bins are evenly spaced along the logarithmically-scaled axis; or the bins may be spaced in another manner. After the data vectors are transformed to the new coordinate system, the first few principal components (i.e., the first few components of the transformed data vectors) are retained for use in training (or using) the RBF model 230. The other components can be disregarded because they primarily represent noise, insignificant variations, or redundancy.

Referring to FIG. 10, plot 400 shows that for an example database of $T_2$ distributions, the first three principal components (labeled 1, 2, 3) account for over 90% of the variances. The curve 402 in the plot 400 shows the cumulative variance after each additional principal component is added. With the understanding that lower variances are more likely to represent noise or redundancy, the components having lower variances can be discarded. In some embodiments, the number of retained components is determined by comparing the ratio:

$$\frac{\sum_{i=p+1}^{n} \lambda_i}{\sum_{i=1}^{n} \lambda_i}$$

with noise-to-signal ratio:

$$\frac{\sigma_{noise}^2}{\sigma_{signal}^2}$$

in the NMR measurement data, where p is the number of retained components. For example, in some embodiments, processed NMR data corresponds to stacked data such that the noise level is below a threshold (e.g., 1 p.u.). Assuming the average porosity is around 30 p.u., the noise-to-signal ratio is about 3 percent. In this example, three principal components of the $T_2$ distribution may be retained. However, it should be appreciated that a greater number of principal components can be retained for use in training or using the RBF model. For example, in some embodiments, four, five, six, or more principal components are retained.

Besides PCA, it should be appreciated that there are other data transform techniques for indirectly representing data such as RBF model training inputs and prediction inputs. Factor analysis is one example of an alternative data transform technique. The use of PCA or another data transform technique for RBF model training inputs and prediction inputs results in the output from trained RBF model 230 being in the same format as the training inputs and prediction inputs. As needed, a data transform is applied to the output from trained RBF model 230 to reconstruct a prediction pore throat size distribution.

Figure 11:
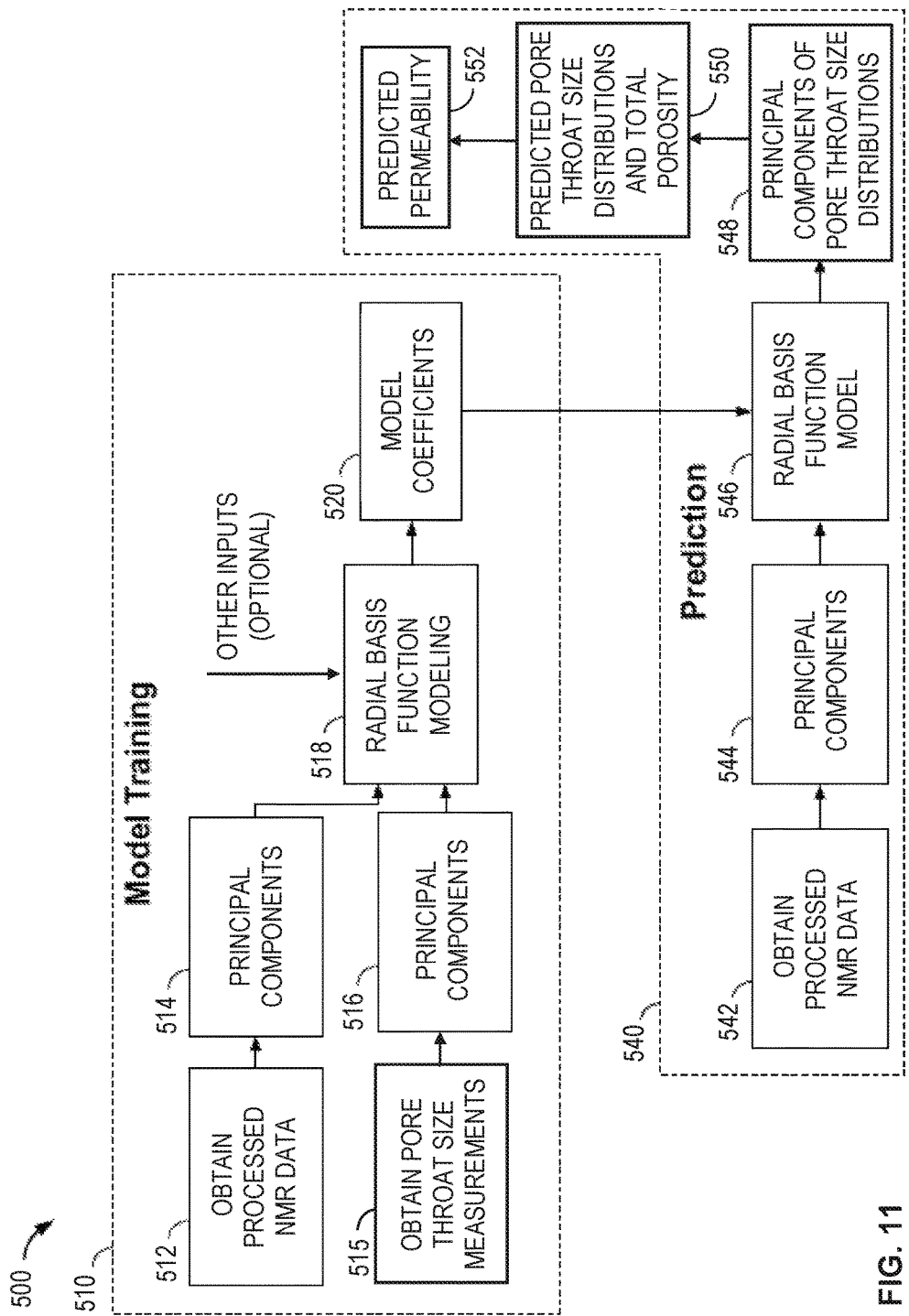
FIG. 11 is a block diagram showing an illustrative process for training and using an RBF model to predict pore throat size distributions.

An example process 500 for training and using an RBF model to predict pore throat size distributions is shown in FIG. 11. The process 500 shown in FIG. 11 includes a model training phase 510 and pore throat size distribution prediction phase 540. In at least some embodiments, the model training phase 510 develops a mapping function based on a training database that includes an NMR relaxation-time distribution data set and a measured pore throat size distribution data set. After the model training phase 510 is complete, the pore throat size distribution prediction phase 540 may predict a pore throat size distribution based on a subsequent NMR relaxation-time distribution data set and the developed mapping function. The process 500 can include additional or different steps, and the steps can be configured as shown or in another manner.

In at least some embodiments, the model training phase 510 includes obtaining processed NMR data at block 512 and obtaining a measured pore throat size distribution at block 515. The processed NMR data obtained at block 512 may correspond to relaxation-time distributions or other processed NMR data derived from NMR measurements collected by a downhole NMR logging tool or a laboratory NMR tool. At block 514, the relaxation-time distributions or other processed NMR data in a training database can be reduced to a set of principal components. Similarly, the measured pore throat size distribution obtained at block 515 can be reduced to a set of set of principal components at block 516.

In at least some embodiments, the principal components corresponding to NMR relaxation-time distributions obtained at block 514 and the principal components corresponding to measured pore throat size distributions obtained at block 516 are used to train an RBF model at modeling block 518. In at least some embodiments, an RBF is a function in the form of $\varphi(\|\vec{x}-\vec{x_c}\|)$, where $\|\vec{x}-\vec{x_c}\|$ is the Euclidean distance between the points $\vec{x}$ and $\vec{x_c}$, and where $\vec{x}$ is the variable and $\vec{x_c}$ is the center of the radial basis function. An RBF model $F(\vec{x})$ can be represented as a linear combination of RBFs. The RBF model can be used to approximate the physical system $f(\vec{x})$ to a certain degree of accuracy, for example, assuming the underlying physical system $f(\vec{x})$ is smooth and continuous.

In at least some embodiments, an RBF model $F(\vec{x})$ is derived at modeling block 518 by interpolating an input-output data set $\{(\vec{x}_i, \vec{y}_i)\}_{i=1}^N$ sampled from an underlying physical system $f(\vec{x})$, where $\{\vec{x}_i\}_{i=1}^N$ is the database of relaxation-time distributions transformed by PCA analysis, and $\{\vec{y}_i\}_{i=1}^N$ are the measured pore throat size data points corresponding to available NMR data. An RBF model can be represented $$F(\vec{x}) = \Sigma_{i=1}^N \vec{w}_i \varphi(\|\vec{x} - \vec{c}_i\|) \qquad \text{Equation (5)}$$

where, $$F(\vec{x}_i) = \vec{y}_i, i = 1, 2, \ldots, N,$$

In this example model, $$\{\vec{w}_i \varphi(\|\vec{x} - \vec{c}_i\|)\}_{i=1}^N \qquad \text{Equation (6)}$$

is a set of weighted radial basis functions, $N$, $\vec{w}_i$, and $\vec{c}_i$ are model coefficients, and $\{(\vec{x}_i, \vec{y}_i)\}_{i=1}^N$ is the input-output training set.

In the above model, the parameters $\{(\vec{c}_i)\}_{i=1}^N$ represent the centers of the RBF model. In some embodiments, the centers correspond to input training parameters obtained from a database of relaxation-time distributions transformed by PCA analysis, principal components of normalized relaxation-time distributions, corresponding total porosities, or combinations of these and other input training parameters. In this case, the RBF model can be represented as:

$$F(\vec{x}) = \Sigma_{i=1}^N \vec{w}_i \varphi(\|\vec{x} - \vec{x}_i\|), \qquad \text{Equation (7)}$$

where $N$, $\vec{w}_i$, and $\vec{x}_i$ are the model coefficients. The function $\varphi$ can be a Gaussian function or another type of smooth function. For example, when the function $\varphi$ is a Gaussian, the matrix associated with the interpolation is well-conditioned, and the RBF inversion has a unique solution. The training operations performed at modeling block 518 generates, for example, model coefficients 520, where the resulting RBF model and its coefficients can be used as a mapping function that predicts the principal components of pore throat size distributions based on subsequent NMR data (e.g., during prediction phase 540).

In at least some embodiments, the model coefficients 520 obtained by modeling block 518 can be determined by interpolation of available training datasets. In some instances, the coefficients $\vec{w}_i$ can be determined by requiring that the interpolation equations be satisfied exactly. For example, the coefficients can be a linear combination of the function values $$\vec{w}_i = \Sigma_{j=1}^N \Phi_{ij}^{-1} \vec{y}_j, \qquad \text{Equation (8)}$$

where $\varphi_{ij}^{-1}$ is the (i, j) element of the inverse of the N×N interpolation matrix In at least some embodiments, the process of predicting pore throat size distributions involves remapping a relaxation-time distribution or other processed NMR data corresponding to a subterranean formation with unknown pore throat size distributions to a new coordinate system identified during RBF model training. That is, the dataset matrix $X_{input}$ can be transformed to the new coordinate system by the operation $T_{input} = X_{input} W_L$, where the transformed matrix $T_{input}$ has l columns. Here, each element $T_{input}(i, k)$ (the element at the $k^{th}$ column, $i^{th}$ row) represents the $k^{th}$ principal component of the $i^{th}$ input relaxation-time distribution, and $W_L$ represents the transformation matrix identified during model training.

Transformed matrix $T_{input}$ can be input into the RBF model, using the model coefficients identified during model training. That is, if $T_{input}$ represents the vector elements of $\vec{x}$, the predicted principal components of pore throat size distributions $F(\vec{x})$ can be determined by:

$$F(\vec{x}) = \Sigma_{i=1}^N \vec{w}_i \varphi(\|\vec{x} - \vec{c}_i\|), \qquad \text{Equation (9)}$$

where $N$, $\vec{w}_i$, and $\vec{c}_i$ are the model coefficients identified during model training. Thus, after model training, the principal components of subsequent pore throat size distributions can be predicted using independently acquired NMR measurements.

In at least some embodiments, the pore throat size prediction phase 540 includes obtaining processed NMR data at block 542. The processed NMR data obtained at block 542 may correspond to relaxation-time distributions or other processed NMR data derived from NMR measurements collected by a downhole NMR logging tool or a laboratory NMR tool. At block 544, the principal components for the processed NMR data are determined. As an example, the principal components at block 544 may be determined based on principal component analysis results from block 514 of the model training phase 510. The principal components determined at block 544 can then be used as an input to an RBF model at prediction block 546. While the example of process 500 applies principal components to the RBF model at prediction block 546, it should be appreciated that other embodiments may apply different types of processed NMR data to the RBF model. Examples of NMR data that may be input to the RBF model include raw NMR measurements, NMR relaxation-time distributions derived from NMR measurements, principal components or factors representing NMR relaxation-time distributions derived from NMR measurements, an arithmetic or geometric means of an NMR relaxation-time distribution derived from NMR measurements, and a ratio of different NMR relaxation-time distributions (e.g., a $T_1/T_2$ distribution) derived from NMR measurements. At prediction block 546, the RBF model may also receive model coefficients identified at block 520 of the model training phase 510.

At block 548, predicted principal components of pore throat size distributions are output from the prediction block 546. At block 550, predicted pore throat size distributions are derived from the predicted principal components of block 548. Further, at block 552, a predicted permeability is derived from the predicted pore throat size distributions determined at block 550. In at least some embodiments, a total porosity is also derived from the predicted pore throat size distributions at block 550. In such case, the predicted permeability derived at block 552 may be a function of total porosity as well as the predicted pore throat size distributions.

Rock permeability is a function of the number of connected channels (or capillaries) and the size of the cross-section of these connected capillaries. Further, the number of connected channels is proportional to void volume, which is dependent on porosity. The connected channels have different cross sections of pore throat; and each channel is expected to have multiple throats with different cross sectional area along the flow passage. The smallest cross section, hereby denoted as $\sigma_m$, is the determining factor for flow. On the other hand, among all channels, the ones with the largest $\sigma_m$ contribute to permeability most significantly. In view of the above factors, the predicted permeability at block 552 may be derived using a permeability equation or model that accounts for porosity and predicted pore throat size distributions. In some embodiments, predicted pore throat size distributions are represented by corresponding geometric mean values, and the porosity is derived from the summation of all components in a given pore throat size distribution. In such case, the permeability values derived at block 552 may be calculated as:

$$k = c\phi^a r_{t,gm}^b,\qquad\text{Equation (10)}$$

where $\phi$ is a predicted total porosity value, where $r_{t,gm}$ is a geometric mean of a predicted pore throat size distribution obtained at block 550, and where a, b, and c are predetermined values. The predicted total porosity can be obtained either as an independent prediction parameter, or as a side-product of the predicted pore throat size distribution. For example, in at least some embodiments, $\phi$ is derived from predicted. pore throat size distributions obtained at block 550. Further, a, b, and c may be derived from measured pore throat size distributions based on regression.

In other embodiments, the permeability values derived at block 552 are calculated as:

$$k = 10^{-d}(r_{t,max})^e \phi^f,\qquad\text{Equation (11)}$$

where $\phi$ is a predetermined total porosity value, where $r_{t,max}$ is a maximum pore throat of a predicted pore throat size distribution obtained at block 550, and where d, e, and f are predetermined values. In this variation, the correlation of pore throat size and permeability is represented by $r_{t,max}$. As explained previously, permeability is largely a function of the largest flow channel, $\sigma_m$. For carbonate systems that have a wide distribution of pore throat sizes, equation 11 may yield a more accurate permeability prediction than equation 10. Meanwhile, equation 10 may be more suitable for pore systems with relatively narrow distribution range of pore throat sizes. In at least some embodiments, $r_{t,max}$ is obtained by predicting a minimum entry pressure from a RBF model trained with the principal components of NMR relaxation-time distributions. Further, $\phi$ may be derived from the predicted pore throat size distribution obtained at block 550. Further, d, e, and f may be derived from the measured pore throat distributions based on regression.

In other embodiments, both $r_{t,max}$ and $r_{t,gm}$ are considered important to permeability, and the permeability prediction equation includes both these control parameters with their exponent weighting factors as an adjustment parameter. In such case, the permeability values derived at block 552 may be calculated as:

$$k = 10^{-g}(r_{t,max})^h(r_{t,gm})^i \phi^j,\qquad\text{Equation (12)}$$

where $r_{t,max}$ is a maximum throat of the predicted pore throat size distributions, where $r_{t,gm}$ is a geometric mean of the predicted pore throat size distribution obtained at block 550 from the predicted principal components output from prediction block 546, where $\phi$ is a total porosity value, and where g, h, i, and j are predetermined values. Again, $r_{t,max}$ may be obtained by predicting a minimum entry pressure from the predicted pore throat size distribution. Further, $\phi$ may be derived from the predicted pore throat size distribution obtained at block 550. Further, g, h, i, and j may be derived from the measured pore throat size distributions based on regression.

In at least some embodiments, predicted pore throat size distributions obtained at block 550 are used to derive pore-type data for a rock sample or along a formation. Example pore-types includes as micro-, meso-, and macro-pore types. The pore-type information obtained from the predicted pore throat size distributions may be reported or displayed as desired. Further, predicted pore throat size distributions obtained at block 550 may be used to obtain a Thomeer capillary pressure equation.

In at least some embodiments, predicted pore throat size validation operations are performed. Such validation operations may, for example, involve comparing predicted pore throat size distributions with measured pore throat size data points using a "leave one out" method, in which a sample from the training data set is taken out and its pore throat size is predicted using the RBF model developed with the rest of the data in the training data set. If predicted pore throat size distributions are within a predetermined threshold (e.g., within order of magnitude of the measured pore throat size data points), the predicted pore throat size distributions may be considered to be acceptable. As needed, RBF model options are adjusted to improve prediction results.

Though more training samples may improve the RBF model used in prediction block 546 in some cases, using more samples as the centers in the RBF model does not necessarily result in better prediction performance in all cases. For instance, in some embodiments, increasing the number of centers in a RBF model may result in an RBF model that over-fits the available training data. Such over-fitting can negatively affect the prediction performance of the RBF model. In different embodiments, the number of samples used for the RBF centers can be selected empirically, or according to other selection criteria. In some cases, all the available training samples are used during the training process, including some instances where forward selection is used to select the centers.

In at least some embodiments, relaxation-time distributions or other processed NMR data used for RBF model training or pore throat size predictions can be normalized. For instance, in some embodiments, relaxation-time distributions can be separated into two parts: the relative shape of the distributions and the summation of the amplitudes of the distributions (i.e., the total porosities). Further, PCA can be applied to the relative shape of the distributions. For the above relaxation-time distributions, the resulting RBF model or pore throat size predictions would be dependent on the relative shape of the distributions and the summation of the amplitudes of the distributions. Example normalization values include 0.5, 1.0, 1.5, 2, 2.5, and so forth.

In at least some embodiments, the RBF model described herein corresponds to an interpolation method, where RBF model performance depends on the quality of the training database. For example, if the measured pore throat size data points of the training database are very noisy and/or if too many centers are used for the interpolation, the RBF model can become overly sensitive to the details of the data, which may result in oscillatory behavior due to over-fitting. These detrimental effects can be mitigated in various ways.

For instance, in order to mitigate the effects of over-fitting, in some embodiments, the RBF model can be regularized according to a cost function that penalizes oscillatory behavior. The input data with noise can be described by:

$$F(\vec{x}_i) = \vec{y}_i + \varepsilon_i,\ i=1, 2, \ldots, N,\qquad\text{Equation (13)}$$

where $$F(\vec{x}) = \sum_{i=1}^{N} \vec{w}_i \varphi(\|\vec{x} - \vec{x}_i\|),\qquad\text{Equation (14)}$$

assuming the centers of the RBF functions are the set of training inputs, and $\epsilon_i$ is the noise in the measurement data. The RBF model can be obtained by minimizing the following cost function:

$$E(F)=\Sigma_{i=1}^{N}(\vec{F}(\vec{x}_i)-\vec{y}_i)^2+\lambda\Sigma_{i=1}^{N}\vec{w}_i^2, \quad \text{Equation (15)}$$

where $$\sum_{i=1}^{N}(\vec{F}(\vec{x}_i)-\vec{y}_i)^2$$

is the fitting error, and $$\sum_{i=1}^{N}\vec{w}_i^2$$

is the regularization term to penalize the oscillations in the fitting. The parameter λ controls the balance between fitting the data and avoiding the penalty, and can be assigned different values depending on the desired fitting behavior. In some embodiments, the value of parameter λ can be determined using generalized cross-validation methods in order to assess the accuracy of the resulting RBF model. Example cross-validation methods include K-fold cross validation, repeated random sub-sampling validation, and leave-one-out cross-validation. Use of regularization for an RBF model decreases the likelihood of over-fitting and susceptibility to noise in the training database compared to a non-regularized RBF model.

In at least some embodiments, in order to mitigate the effects of over-fitting, the centers of RBF model can be derived from only a subset of available relaxation-time distributions or other processed NMR data in a training database. That is, instead of using all the data of the training database for the centers of the RBF model, only a subset of the data set is selected for the centers of the RBF model. For example, in some embodiments, the goal of this selection is to find a subset which can explain most, but not all, of the variation in the training set, with the goal of avoiding over-fitting noise. In some instances, a subset of the training samples are used for the centers of the RBF model, and all the training samples (including the subset) are used to compute other parameters (e.g., the weights) of the RBF model.

An optimal or otherwise acceptable subset of training data used for the centers of the RBF model can be selected using various techniques. For instance, in the forward selection technique, individual centers can be added to the model one at a time, and each center can be tested for inclusion in the model. The most significant of these centers can then be added to the model.

An example embodiment of forward selection can be performed, where C is the collection of the centers of the RBF model, C1 is the collection of data which are candidates of the centers of the RBF model, and where initially C is empty and C1 is the training database. For each sample center in the collection C1, an RBF model can be constructed whose centers are the selected samples from C1 and the samples in the collection C. A sample center with the smallest SSE (i.e., is the sum of squared errors over all the sample centers in the training data set) is removed from C1 and added into C. This can be repeated, for example, until C1 is empty, or certain stop criteria is met.

There are several criteria which can be used to stop the selection process. For instance, the number of selected centers can be selected in order to minimize criteria such as the Bayesian information criterion (BIC), or the generalized cross-validation (CGV) criterion. For example, in a non-regularized RBF model, a CGV criterion can be represented as $$GCV = \frac{N}{(N-M)^2}SSE, \quad \text{Equation (16)}$$

where N is the number of sample centers in the training database and M is the number of centers in the RBF model. In another example, in a non-regularized RBF model, a BIC can be represented as $$BIC = \frac{N+(\ln(N)-1)M}{N(N-M)}SSE. \quad \text{Equation (17)}$$

Accordingly, in some embodiments, the numbers of centers that minimize the GCV and/or BIC values may be selected for the RBF model. Use of forward selection for an RBF model decreases the likelihood of over-fitting and susceptibility to noise in the training database compared to an RBF model without forward selection. In some embodiments, backward selection can be used instead of forward selection. As an example, for an RBF model whose centers are made of all the samples in the training database, individual centers can be removed from the model one at a time, and each center can be tested for subtraction from the model.

In at least some embodiments, multiple techniques can be simultaneously used to reduce over-fitting. For example, in some embodiments, regularization is applied at each step of the forward selection method. In another example, in order to reduce computation requirements, regularization is applied to the RBF model after centers are selected using forward selection. Use of multiple techniques together decreases the likelihood of over-fitting and susceptibility to noise in the training database compared to an RBF model that does not use multiple techniques.

It should be appreciated that an RBF model developed using training data from one well can be used to predict pore throat size distributions from NMR data corresponding to another well. The accuracy of pore throat size distribution prediction depends on the data of the training database and whether the two wells have similar characteristics. Further, the RBF model developed using the training data from one well can be validated by predicting pore throat size distributions for another well. In such case, both wells have their own measured pore throat size distributions and NMR data. Alternatively, the accuracy of an RBF model can be tested using the "leave one out" method and/or by dividing the data of the training database into two sets: one set for use in RBF model development, and another set for validation.

Figures 12A, 12B, 12C:
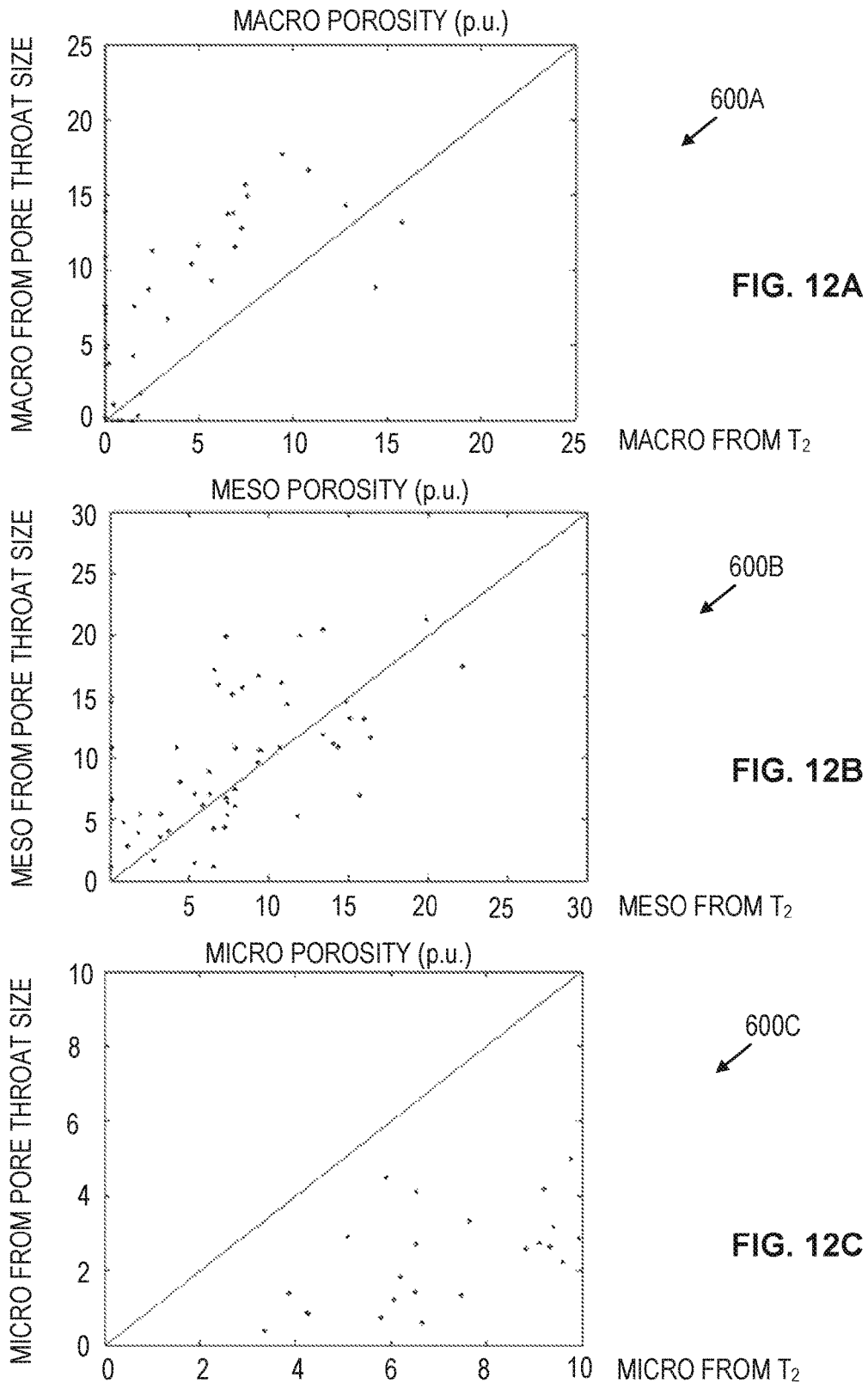
FIGS. 12A-12C are plots comparing porosities obtained from measured pore throat size distributions with porosities obtained by applying $T_2$ cutoffs to $T_2$ distributions.

FIGS. 12A-12C are plots 600A-600C comparing porosities obtained from measured pore throat size distributions with porosities obtained by applying $T_2$ cutoffs to $T_2$ distributions. Specifically, plot 600A of FIG. 12A shows macro porosity data, plot 600B of FIG. 12B shows meso porosity data, and plot 600C of FIG. 12C shows micro porosity data. As can be seen in plots 600A-600C, porosities obtained by applying $T_2$ cutoffs to $T_2$ distributions do not match porosities obtained from measured pore throat size distributions. In particular, the micro porosity values do not match.

Figures 13A, 13B, 13C:
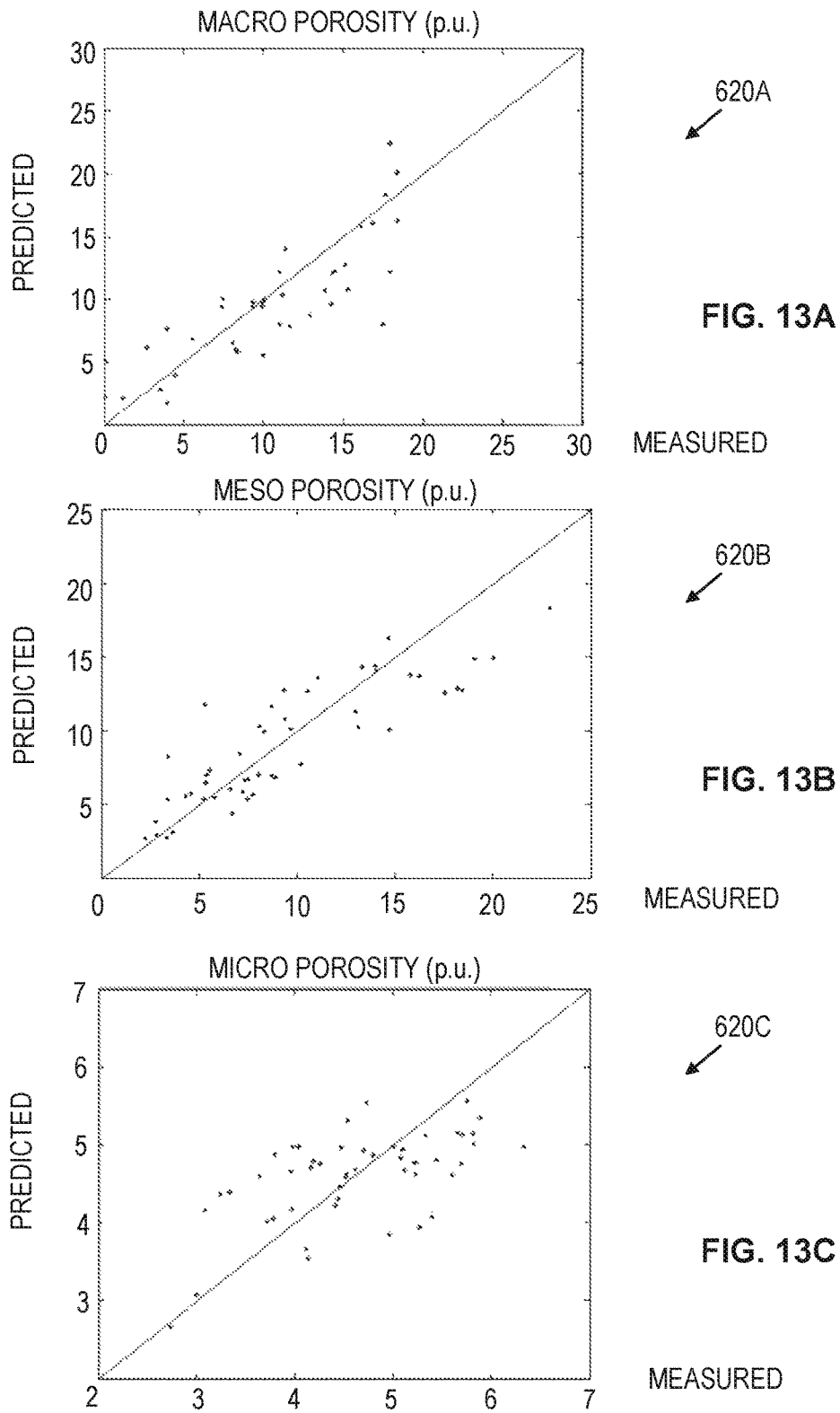
FIGS. 13A-13C are plots comparing porosities obtained from predicted pore throat size distributions with porosities obtained from measured pore throat size distributions

FIGS. 13A-13C are plots 620A-620C comparing porosities obtained from pore throat size distribution prediction results of an RBF model with porosities obtained from measured pore throat size distributions. Specifically, plot 620A of FIG. 13A shows macro porosity data, plot 620B of FIG. 13B shows meso porosity data, and plot 620C of FIG. 13C shows micro porosity type data. As can be seen in plots 620A-620C, porosities obtained from pore throat size distribution prediction results of an RBF model match with porosities obtained from measured pore throat size distribution better than the results obtained from applying $T_2$ cutoffs to $T_2$ distributions.

Figures 14, 15:
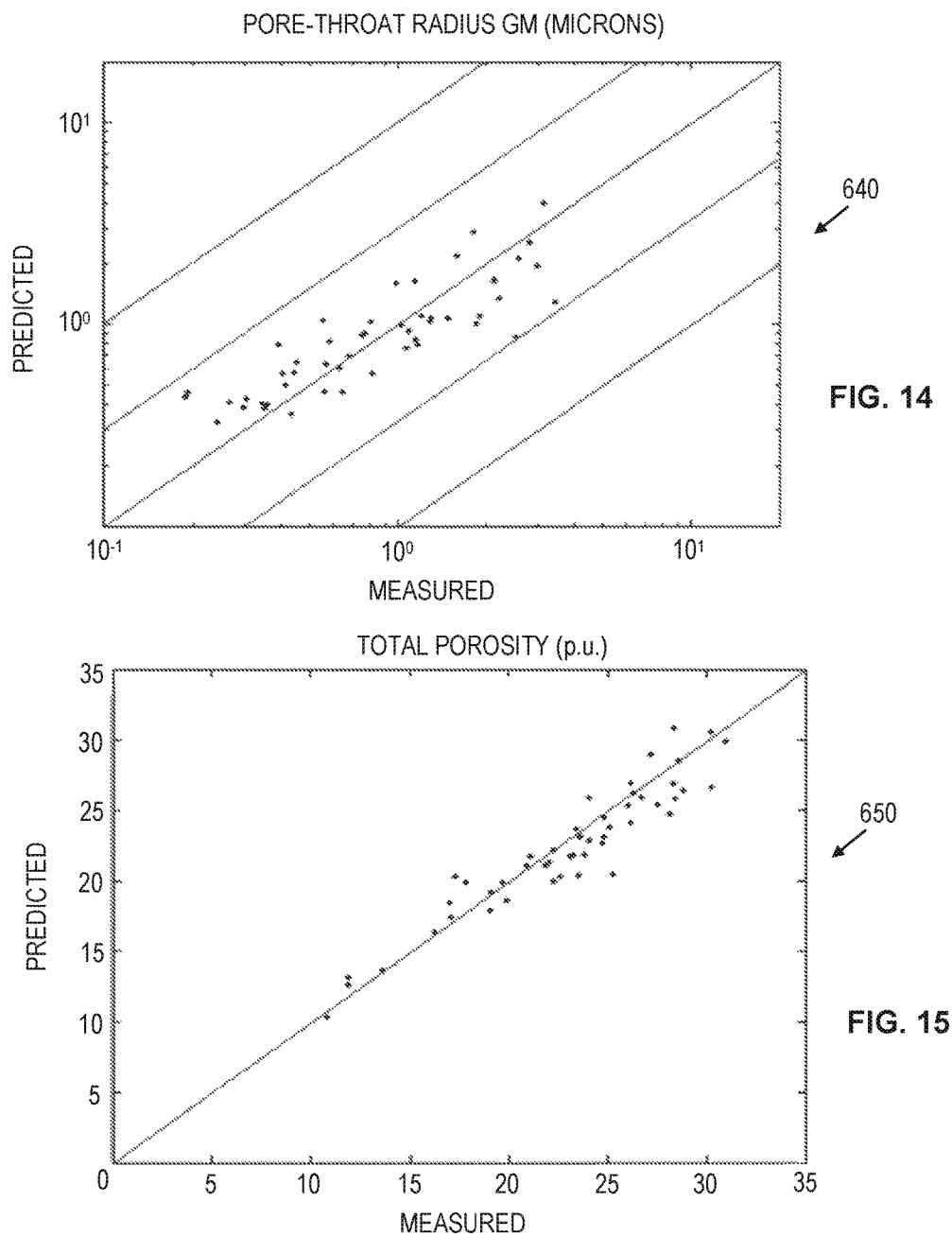
FIGS. 14 and 15 are plots showing various properties of predicted pore throat sizes compared to properties of measured pore throat sizes.

FIG. 14 is a plot 640 showing a comparison of the geometric means (GM) for predicted pore throat sizes and measured pore throat sizes. Meanwhile, plot 650 of FIG. 15 shows a comparison of total porosity corresponding to measured and predicted pore throat sizes. The predicted pore throat sizes related to plots 640 and 650 correspond to predicted pore throat size distributions obtained by applying NMR data to a trained RBF model as described herein. As shown in plots 640 and 650, the predicted pore throat sizes and derived parameters (e.g., total porosity) have an acceptable degree of accuracy relative to measured pore throat sizes and parameters derived from measured pore throat sizes.

In different embodiments, a predicted pore throat size distribution data set or related values (e.g., a predicted pore throat size distribution, the geometric mean of a predicted pore throat size distribution, related porosity values, related permeability values) may be plotted in the form of a chart or log (see e.g., 13A-13C, 14, 15, or a pore throat size distribution curve as in FIG. 5B). Such plots or related values may be displayed to an operator via a computer monitor, a tablet, or other processing device with a user interface. Based on such plots and/or other information, an operator may select to adjust RBF modeling and pore throat size prediction options, resulting in plots with modified predicted pore throat size distributions or derived parameters. Examples of adjustable settings include PCA parameters, RBF modeling parameters, data normalization, training data selection criteria, curve fitting parameters, etc. Further, such plots may be reported to a customer or otherwise used to generate a report for a customer.

Additionally or alternatively, a predicted pore throat size distribution data set or related values (e.g., a predicted pore throat size distribution, the geometric mean of a predicted pore throat size distribution, related porosity values, related permeability values) may be provided as input to a simulation system that predicts, for example, the flow of fluids in a reservoir as a function of time. Such simulations are used for reservoir planning and may influence decisions regarding the number of wells, the placement/arrangement of injection wells, the placement/arrangement of production wells, the placement/arrangement of monitoring wells, fracturing operations, enhanced oil recovery (EOR) operations, and so forth.

Figure 16:
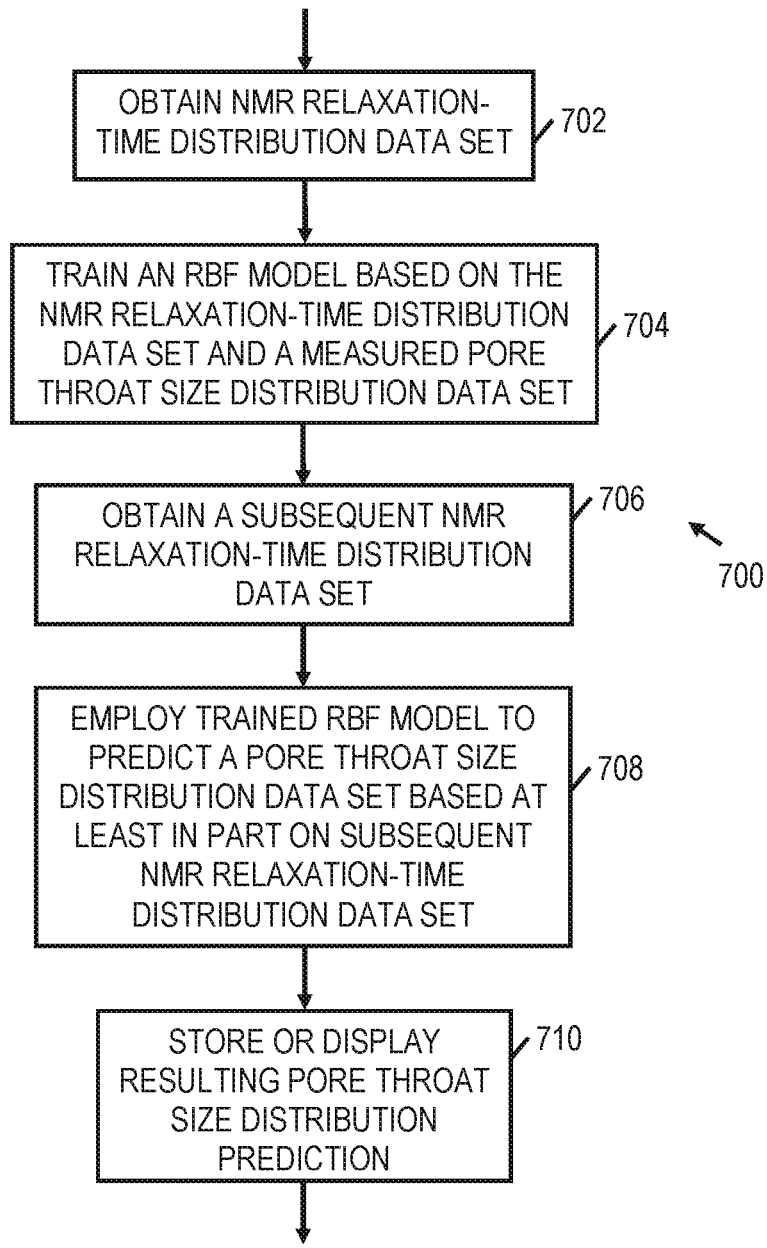
FIG. 16 is a flowchart showing an illustrative pore throat size distribution prediction method.

FIG. 16 shows an illustrative pore throat size prediction method 700. At block 702, an NMR relaxation-time distribution data set is obtained. As described herein, NMR relaxation-time distribution data set may correspond directly or indirectly to an NMR relaxation-time distribution obtained from downhole NMR logging tools or laboratory NMR tools for a downhole formation volume or rock sample volume. In at least some embodiments, the NMR relaxation-time distribution data set corresponds to data transform values (principal components or factors) of an NMR relaxation-time distribution. At block 704, an RBF model is trained based on the NMR relaxation-time distribution data set and a measured pore throat size distribution data set. The measured pore throat size distribution data set may correspond directly or indirectly to a measured pore throat size distribution obtained from laboratory tests performed on a rock sample volume. In at least some embodiments, the measured pore throat size distribution data set corresponds to data transform values (principal components or factors) of a measured pore throat size distribution.

At block 706, a subsequent NMR relaxation-time distribution data set is obtained. The subsequent NMR relaxation-time distribution data set and the NMR data set using for training the RBF model may be obtained from the same NMR tool or different NMR tools. The subsequent NMR relaxation-time distribution data set may correspond directly or indirectly to an NMR relaxation-time distribution obtained from downhole NMR logging tools or laboratory NMR tools for a downhole formation volume or rock sample volume. In at least some embodiments, the subsequent NMR relaxation-time distribution data set corresponds to data transform values (principal components or factors) of an NMR relaxation-time distribution.

At block 708, the trained RBF model is employed to predict a pore throat size distribution data set based at least in part on the subsequent NMR relaxation-time distribution data set. At block 710, a predicted pore throat size distribution or related values resulting from the predicted pore throat size distribution data set is stored or displayed (e.g., the plots of FIGS. 13A-13C, 14, 15, a pore throat size distribution curve as in FIG. 5B, a log plotting the geometric mean of predicted pore throat size distributions, or a log of permeability values derived from predicted pore throat size distributions). As needed, a data transform is applied to the predicted pore throat size distribution data set to construct a predicted pore throat size distribution or related values. As needed, adjustments are made to the RBF model, the type of training data used, and/or the input data for a trained RBF model. Such adjustments may be determined at least in part from displaying plots or related data. Additionally or alternatively, stored values for predicted pore throat size distributions related values may be provided as input to a simulator that predicts, for example, fluid flows in a reservoir as a function of time.

In accordance with at least some embodiments, the disclosed methods and systems related to predicting pore throat size distributions may be implemented in digital electronic circuitry, or in computer software, firmware, or hardware, including the structures disclosed in this specification and their structural equivalents, or in combinations of one or more of them. Computer software may include, for example, one or more modules of instructions, encoded on computer-readable storage medium for execution by, or to control the operation of, a data processing apparatus. Examples of a computer-readable storage medium include random access memory (RAM) devices, read only memory (ROM) devices, optical devices (e.g., CDs or DVDs), disk drives, etc.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read-only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 17:
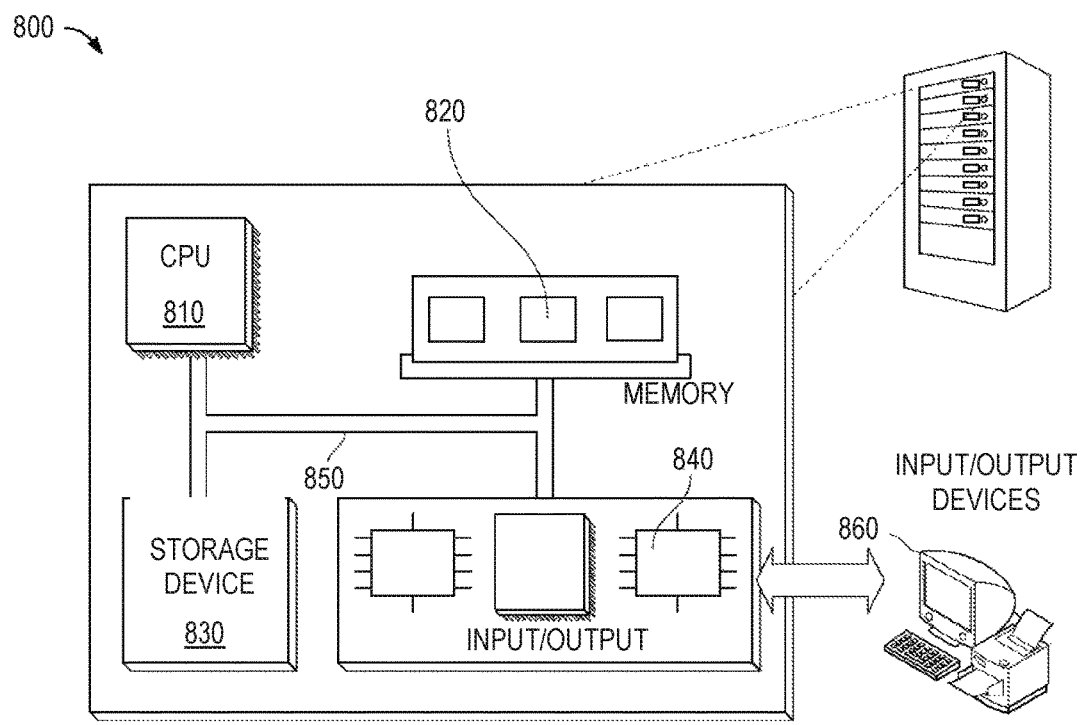
FIG. 17 is a diagram showing an illustrative computer system.

FIG. 17 shows an illustrative computer system 800. The computer system 800 may correspond to the computer system 42 mentioned in FIG. 1 and/or another computer system involved with collecting NMR measurements, processing NMR measurements, selecting training data from a database, constructing an RBF model, using the RBF model to predict pore throat size distributions, deriving other parameters (e.g., total porosity values, permeability values, pore types) from the predicted pore throat size distributions, and/or displaying logs or reports of predicted pore throat size distributions or derived parameters as described herein. The system 800 includes a processor 810, a memory 820, a storage device 830, and an input/output device 840. Each of the components 810, 820, 830, and 840 can be interconnected, for example, using a system bus 850. The processor 810 is capable of processing instructions for execution within the system 800. In some embodiments, the processor 810 is a single-threaded processor, a multi-threaded processor, or another type of processor. The processor 810 is capable of processing instructions stored in the memory 820 or on the storage device 830. The memory 820 and the storage device 830 can store information within the computer system 800.

The input/output device 840 provides input/output operations for the system 800. In some embodiments, the input/output device 840 can include one or more network interface devices, e.g., an Ethernet card; a serial communication device, e.g., an RS-232 port; and/or a wireless interface device, e.g., an 802.11 card, a 3G wireless modem, a 4G wireless modem, etc. In some embodiments, the input/output device can include driver devices configured to receive input data and send output data to other input/output devices, e.g., keyboard, printer and display devices 860. In some embodiments, mobile computing devices, mobile communication devices, and other devices can be used.

The disclosed options for predicting pore throat size distributions should not be construed as limitations on the scope of what may be claimed, but rather as descriptions of features specific to particular examples. Certain features that are described in this specification in the context of separate embodiments can also be combined. Conversely, various features that are described in the context of a single embodiment can also be implemented in multiple embodiments separately or in any suitable combination.

Embodiments disclosed herein include:

A: A method that comprises obtaining an NMR relaxation-time distribution data set, training an RBF model based on the NMR relaxation-time distribution data set and a measured pore throat size distribution data set, obtaining a subsequent NMR relaxation-time distribution data set, employing the trained RBF model to predict a pore throat size distribution data set based at least in part on the subsequent NMR relaxation-time distribution data set, and storing or displaying a predicted pore throat size distribution corresponding to the predicted pore throat size distribution data set. The predicted pore throat size distribution is associated with a rock sample or subsurface formation volume.

B: A system that comprises at least one processor and a memory in communication with the at least one processor and storing instructions. When executed, the instructions cause the at least one processor to obtain an NMR relaxation-time distribution data set, and to train an RBF model based on the NMR relaxation-time distribution data set and a measured pore throat size distribution data set. When executed, the instructions cause the at least one processor to obtain a subsequent NMR relaxation-time distribution data set, and to employ the trained RBF model to predict a pore throat size distribution data set based at least in part on the subsequent NMR relaxation-time distribution data set. When executed, the instructions also cause the at least one processor to store or display a predicted pore throat size distribution corresponding to the predicted pore throat size distribution data set. The predicted pore throat size distribution is associated with a rock sample or subsurface formation volume.

Each of the embodiments, A and B, may have one or more of the following additional elements in any combination. Element 1: further comprising displaying a log that plots the predicted pore throat size distribution or permeability values derived at least in part from the predicted pore throat size distribution as a function of measured depth. Element 2: further comprising using the predicted pore throat size distribution to calculate permeability values as:

$$k = c\phi^a r_{t,gm}^b,$$

where $\phi$ is a total porosity value, where $r_{t,gm}$ is a geometric mean of the predicted pore throat size distribution, and where a, b, and c are predetermined values. Element 3: further comprising using the predicted pore throat size distribution to calculate permeability values as:

$$k = 10^{-d}(r_{t,max})^e \phi^f,$$

where $\phi$ is a total porosity value, where $r_{t,max}$ is a maximum value of the predicted pore throat size distribution, and where d, e, and f are predetermined values. Element 4: further comprising using the predicted pore throat size distribution to calculate permeability values as:

$$k = 10^{-g}(r_{t,max})^h (r_{t,gm})^i \phi^j,$$

where $r_{t,max}$ is a maximum pore throat of the predicted pore throat size distribution, where $r_{t,gm}$ is a geometric mean of the predicted pore throat size distribution, where $\phi$ is a total porosity value, and where g, h, i, and j are predetermined values. Element 5: wherein the NMR relaxation-time distribution data set, the subsequent NMR relaxation-time distribution data set, the measured pore throat size distribution data set, and the predicted pore throat size distribution data set correspond to principal component analysis (PCA) coefficients. Element 6: wherein the trained RBF model uses forward selection to predict the pore throat size distribution data set. Element 7: further comprising predicting a minimum entry pressure or total porosity based on the predicted pore throat size distribution and using the predicted minimum entry pressure or total porosity to calculate permeability values. Element 8: further comprising deriving pore-type data using the predicted pore throat size distribution. Element 9: wherein obtaining the NMR relaxation-time distribution data set comprises collecting NMR measurements by a downhole logging tool, deriving an NMR relaxation-time distribution based on the collected NMR measurements, and determining principal components or factors of the NMR relaxation-time distribution. Element 10: further comprising assessing a quality of the predicted pore throat size distribution and re-training the RBF model if the quality is determined to be below a threshold.

Element 11: wherein the trained RBF model uses forward selection to predict the pore throat size distribution data set. Element 12: wherein the instructions, when executed, further cause the at least one processor to calculate permeability values as a function of at least one of a geometric mean of the predicted pore throat size distribution and a maximum pore throat of the predicted pore throat size distribution. Element 13: wherein the instructions, when executed, further cause the at least one processor to predict a minimum entry pressure based on the predicted pore throat size distribution and to use the predicted minimum entry pressure to calculate permeability values. Element 14: wherein the instructions, when executed, further cause the at least one processor to predict a total porosity based on the predicted pore throat size distribution and to use the predicted total porosity to calculate permeability values. Element 15: wherein the NMR relaxation-time distribution data set, the subsequent NMR relaxation-time distribution data set, the measured pore throat size distribution data set, and the predicted pore throat size distribution data set correspond to principal component analysis (PCA) coefficients. Element 16: wherein the instructions, when executed, further cause the at least one processor to provide a user interface that enables an operator to adjust prediction results by adjusting at least one item selected from the list consisting of RBF model training options, RBF model options, and principal component analysis (PCA) options. Element 17: further comprising a monitor in communication with the at least one processor to display a log that plots the predicted pore throat size distribution or permeability values derived at least in part from the predicted pore throat size distribution as a function of measured depth. Element 18: further comprising a downhole NMR logging tool in communication with the at least one processor to collect NMR measurements from which the obtained NMR relaxation-time distribution data set is derived.

Numerous variations and modifications will become apparent to those skilled in the art once the above disclosure is fully appreciated. It is intended that the following claims be interpreted to embrace all such variations and modifications.

What is claimed is:

1. A method that comprises:
    obtaining a nuclear magnetic resonance (NMR) relaxation-time distribution data set and a measured pore throat size distribution data set;
    determining principal components associated with the NMR relaxation-time distribution data set and the measured pore throat size distribution data set;
    training, by at least one processor, a radial basis function (RBF) model based on at least some of the principal components of the NMR relaxation-time distribution data set and at least some principal components of the measured pore throat size distribution data set;
    obtaining a subsequent NMR relaxation-time distribution data set from measurements collected by a downhole NMR logging tool while deployed in a borehole, wherein the downhole NMR logging tool includes a receiver which receives magnetic resonance signals in a formation based on transmission of a plurality of RF pulses in the formation, a transmitter which transmits the plurality of RF pulses in the formation, and NMR spectrometry components;

determining principal components associated with the subsequent NMR relaxation-time distribution data set;

employing, by at least one processor, the trained RBF model to predict principal components of a pore throat size distribution data set based at least in part on some of the principal components of the subsequent NMR relaxation-time distribution data set, wherein the trained RBF is based on a linear combination of Gaussian basis functions; and wherein the trained RBF maps some of the principal components of the subsequent NMR relaxation-time distribution data set to the principal components of the pore throat size distribution data set;

deriving a predicted pore throat size distribution based at least in part on the predicted principal components of the pore throat size distribution data set; and displaying, by an output device, the predicted pore throat size distribution based at least in part on the predicted principal components of the pore throat size distribution data set, wherein the predicted pore throat size distribution is associated with a rock sample or subsurface formation volume.

2. The method of claim 1, further comprising displaying a log that plots the predicted pore throat size distribution or permeability values derived at least in part from the predicted pore throat size distribution as a function of measured depth.

3. The method of claim 1, further comprising using the predicted pore throat size distribution to calculate permeability values as:

$$k = c\varphi^a r_{t,gm}^b,$$

where $\varphi$ is a total porosity value, where $r_{t,gm}$ is a geometric mean of the predicted pore throat size distribution, and where a, b, and c are predetermined values.

4. The method of claim 1, further comprising using the predicted pore throat size distribution to calculate permeability values as:

$$k = 10^{31\ d}(r_{t,max})^e \varphi^f,$$

where $\varphi$ is a total porosity value, where $r_{t,max}$ is a maximum pore throat of the predicted pore throat size distribution, and where d, e, and f are predetermined values.

5. The method of claim 1, further comprising using the predicted pore throat size distribution to calculate permeability values as:

$$k = 10^{-g}(r_{t,max})^h (r_{t,gm})^i \varphi^j,$$

where $r_{t,max}$ is a maximum pore throat of the predicted pore throat size distribution, where $r_{t,gm}$ is a geometric mean of the predicted pore throat size distribution, where $\varphi$ is a total porosity value, and where g, h, i, and j are predetermined values.

6. The method of claim 1, wherein the trained RBF model uses forward selection to predict the pore throat size distribution data set.

7. The method of claim 1, further comprising predicting a minimum entry pressure or total porosity based on the predicted pore throat size distribution and using the predicted minimum entry pressure or total porosity to calculate permeability values.

8. The method of claim 1, further comprising deriving pore-type data using the predicted pore throat size distribution.

9. The method of claim 1, wherein obtaining the measured NMR relaxation-time distribution data set comprises:
    collecting NMR measurements by a downhole logging tool;
    deriving an NMR relaxation-time distribution based on the collected NMR measurements; and
    determining principal components or factors of the NMR relaxation-time distribution.

10. The method of claim 1, further comprising assessing a quality of the predicted pore throat size distribution and re-training the RBF model if the quality is determined to be below a threshold.

11. The method of claim 1, further comprising selecting at least some of the principal components of the NMR relaxation-time distribution data set from the principal components of the NMR relaxation time distribution data set based on a proportion of (i) variances associated with principal components other than the at least some of the principal components of the NMR relaxation-time distribution data; and (ii) variances associated with the principal components of the NMR relaxation-time distribution data.

12. The method of claim 1, wherein the proportion is compared to a noise-to-signal ratio to select the at least some of the principal components of the NMR relaxation-time distribution data set.

13. A system that comprises:
    at least one processor;
    a memory in communication with the at least one processor, the memory to store instructions that, when executed, cause the at least one processor to:
        obtain a nuclear magnetic resonance (NMR) relaxation-time distribution data set and a measured pore throat size distribution data set;
        determine principal components associated with the NMR relaxation-time distribution data set and the measured pore throat size distribution data set;
        train a radial basis function (RBF) model based on at least some of the principal components of the NMR relaxation-time distribution data set and at least some of the principal components of the measured pore throat size distribution data set;
        obtain a subsequent NMR relaxation-time distribution data set;
        determine principal components associated with the subsequent NMR relaxation-time distribution data set;
        employ the trained RBF model to predict principal components of a pore throat size distribution data set based on at least some of principal components of the subsequent NMR relaxation-time distribution data set; wherein the trained RBF is based on a linear combination of Gaussian basis functions; and wherein the trained RBF maps some of the principal components of the subsequent NMR relaxation-time distribution data set to the principal components of the pore throat size distribution data set;
        deriving a predicted pore throat size distribution based at least in part on the predicted principal components of the predicted pore throat size distribution data set; and
        display the predicted pore throat size distribution based at least in part on the predicted principal components of the pore throat size distribution data set, wherein the predicted pore throat size distribution is associated with a rock sample or subsurface formation volume; and a downhole NMR logging tool having a transmitter which transmits a plurality of RF pulses in a formation, a receiver which receives magnetic resonance signals in the formation based on the transmitted plurality of RF pulses, and NMR spectrometer components, wherein the subsequent NMR relaxation-time distribution data set is obtained using measurements collected by the downhole NMR logging tool while deployed in a borehole.

14. The system of claim 13, wherein the trained RBF model uses forward selection to predict the pore throat size distribution data set.

15. The system of claim 13, wherein the instructions, when executed, further cause the at least one processor to calculate permeability values as a function of at least one of a geometric mean of the predicted pore throat size distribution and a maximum pore throat of the predicted pore throat size distribution.

16. The system of claim 13, wherein the instructions, when executed, further cause the at least one processor to predict a minimum entry pressure based on the predicted pore throat size distribution and to use the predicted minimum entry pressure to calculate permeability values.

17. The system of claim 13, wherein the instructions, when executed, further cause the at least one processor to predict a total porosity based on the predicted pore throat size distribution and to use the predicted total porosity to calculate permeability values.

18. The system of claim 13, wherein the instructions, when executed, further cause the at least one processor to provide a user interface that enables an operator to adjust prediction results by adjusting at least one item selected from the list consisting of RBF model training options, RBF model options, and principal component analysis (PCA) options.

19. The system of claim 13, further comprising a monitor in communication with the at least one processor to display a log that plots the predicted pore throat size distribution or permeability values derived at least in part from the predicted pore throat size distribution as a function of measured depth.

20. The system of claim 13, further comprising a laboratory or downhole NMR unit comprising a transmitter, a receiver, and NMR spectrometer components, wherein the downhole NMR unit is to collect NMR measurements from which the obtained NMR relaxation-time distribution data set used to train the RBF model is derived.

21. The system of claim 13, further comprising instructions stored in memory that, when executed, cause the at least one processor to select at least some of the principal components of the NMR relaxation-time distribution data set from the principal components of the NMR relaxation time distribution data set based on a proportion of (i) variances associated with principal components other than the at least some of the principal components of the NMR relaxation-time distribution data; and (ii) variances associated with the principal components of the NMR relaxation-time distribution data.

22. The system of claim 13, wherein the proportion is compared to a noise-to-signal ratio to select the at least some of the principal components of the NMR relaxation-time distribution data set.

* * * * *